United States Patent
Deisenroth et al.

(10) Patent No.: US 10,098,830 B2
(45) Date of Patent: *Oct. 16, 2018

(54) ORAL CARE COMPOSITIONS

(71) Applicant: BASF SE, Ludwigshafen (DE)

(72) Inventors: Ted Deisenroth, Brookfield, CT (US); Glen Thomas Cunkle, Stamford, CT (US); Lauren Junker, Somerville, NJ (US); Michael Kuepfert, White Plains, NY (US); Paul Odorisio, Leonia, NJ (US); Steven N. Saunders, White Plains, NY (US); Vishal Ramnarine, Clifton, NJ (US); Neethu Abraham, New Rochelle, NY (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/302,940

(22) PCT Filed: Apr. 7, 2015

(86) PCT No.: PCT/US2015/024656
§ 371 (c)(1),
(2) Date: Oct. 7, 2016

(87) PCT Pub. No.: WO2015/157241
PCT Pub. Date: Oct. 15, 2015

(65) Prior Publication Data
US 2017/0143612 A1    May 25, 2017

Related U.S. Application Data

(60) Provisional application No. 61/977,713, filed on Apr. 10, 2014, provisional application No. 61/977,721, filed on Apr. 10, 2014.

(51) Int. Cl.
| | |
|---|---|
| *A61K 8/34* | (2006.01) |
| *A61K 8/36* | (2006.01) |
| *A61K 8/362* | (2006.01) |
| *A61K 8/72* | (2006.01) |
| *A61Q 11/00* | (2006.01) |
| *A61K 8/85* | (2006.01) |
| *A61K 8/73* | (2006.01) |
| *A61K 8/88* | (2006.01) |
| *A61K 8/02* | (2006.01) |
| *C08G 63/668* | (2006.01) |
| *C08G 63/12* | (2006.01) |
| *C08B 3/12* | (2006.01) |
| *C08G 63/685* | (2006.01) |

(52) U.S. Cl.
CPC ............. *A61K 8/85* (2013.01); *A61K 8/0204* (2013.01); *A61K 8/731* (2013.01); *A61K 8/733* (2013.01); *A61K 8/88* (2013.01); *A61Q 11/00* (2013.01); *C08B 3/12* (2013.01); *C08G 63/12* (2013.01); *C08G 63/668* (2013.01); *C08G 63/685* (2013.01)

(58) Field of Classification Search
None
See application file for complete search history.

(56) References Cited

U.S. PATENT DOCUMENTS

| | | |
|---|---|---|
| 2003/0152524 A1 | 8/2003 | Eshita |
| 2006/0177416 A1 | 8/2006 | Turnell et al. |
| 2011/0008277 A1* | 1/2011 | Bruggeman ............ A61L 27/16 424/78.37 |
| 2011/0213036 A1 | 9/2011 | Park et al. |
| 2013/0089737 A1* | 4/2013 | Sannino ................... C08B 3/12 428/402 |
| 2013/0095045 A1 | 4/2013 | Groves et al. |
| 2013/0296761 A1* | 11/2013 | Goto .................... A61K 9/0014 602/54 |
| 2014/0027669 A1 | 1/2014 | Detering et al. |

FOREIGN PATENT DOCUMENTS

| | | | |
|---|---|---|---|
| EP | 2666517 A1 | 11/2013 | |
| WO | 2007061794 A2 | 5/2007 | |
| WO | 2008069622 A1 | 6/2008 | |
| WO | WO 2009/021701 * | 2/2009 | ............ C08B 15/10 |
| WO | 2009099455 A1 | 8/2009 | |
| WO | 2013072932 A2 | 5/2013 | |

OTHER PUBLICATIONS

PCT, International Preliminary Report on Patentability and Written Opinion of the International Searching Authority for PCT/US2015/024656, dated Jul. 27, 2015, 9 pages.
PCT, International Preliminary Report on Patentability and Written Opinion of the International Searching Authority for PCT/US2015/024681, dated Jun. 29, 2015, 8 pages.
Richard T. Tran et al., "Recent Developments on Citric Acid Derived Biodegradable Elastomers", Recent Patents on Biomedical Engineering, Nov. 2009, vol. 2, 12 pages.
Joost P. Bruggeman et al., "Biodegradable Xylitol-Based Polymers", 2008 Wiley-VCH Verlag GmbH & Co. KGaA, Weinheim, Apr. 21, 2008, 6 pages.
Andréa Gonçalves Antonio, "Caries preventive effects of xylitol-based candies and lozenges: a systematic review", Journal of Public Health Dentistry 71 (2011) pp. 117-124, American Association of Public Health Dentistry.

(Continued)

*Primary Examiner* — Brian Gulledge
(74) *Attorney, Agent, or Firm* — Lowenstein Sandler LLP

(57) ABSTRACT

The application relates to oral care compositions comprising substantive polyesters formed from xylitol, polycarboxylic acids (or esters, acid halides or anhydrides thereof) and optionally arginine. The formed polyesters or polyesteramides are active in biofilm inhibition and dissolution to maintain clean teeth.

11 Claims, No Drawings

(56) References Cited

OTHER PUBLICATIONS

Extended European Search Report for PCT/US2015/024656, dated Apr. 8, 2017, 9 pages.

* cited by examiner

ORAL CARE COMPOSITIONS

This application is a U.S. national stage of international application number PCT/US2015/024656, filed Apr. 7, 2015, which claims benefit of U.S. provisional application Nos. 61/977,721 and 61/977,713, both filed on Apr. 10, 2014, each of which are incorporated herein by reference in their entireties.

FIELD OF INVENTION

The application relates to oral care compositions comprising substantive polyesters formed from xylitol, polycarboxylic acids (or esters, acid halides or anhydrides thereof) and optionally arginine. The formed polyesters or polyesteramides are active in biofilm inhibition and dissolution to maintain clean teeth.

BACKGROUND

Dental plaque is present to some degree in the form of a film on virtually all dental surfaces. It is a byproduct of microbial growth, and comprises a dense microbial layer consisting of a mass of microorganisms embedded in a polysaccharide matrix. It is reported that plaque adheres firmly to dental surfaces and is removed only with difficulty even through a rigorous brushing regimen. Moreover, plaque rapidly re-forms on the tooth surface after it is removed. Plaque may form on any part of the tooth surface, and is found particularly at the gingival margin, in cracks in the enamel, and on the surface of dental calculus. The problem associated with the formation of plaque on the teeth lies in the tendency of plaque to build up and eventually produce gingivitis, periodontitis and other types of periodontal disease, as well as dental caries, bad breath (halitosis) and dental calculus.

As plaque is formed by oral bacteria, a wide variety of antibacterial agents have been proposed to retard plaque formation and the oral infections associated with plaque formation. For example, halogenated hydroxydiphenyl ether compounds such as triclosan are well known to the art for their antibacterial activity and have been used in oral compositions to counter plaque formation by bacterial accumulation in the oral cavity.

Xylitol is also well known to inhibit the growth of *Streptococcus mutans* an oral bacteria implicated in plaque formation, and that this inhibition causes reduced acid formation which in turn is believed to inhibit caries formation. In the case of xylitol, because of its high water solubility the compound is quickly removed from the oral site, thus having a limited inhibitory effect upon reduced acid formation from *S. mutans*.

These antibacterial agents which work to reduce plaque formation by temporary reduction in the population of oral bacteria have numerous disadvantages when incorporated into commercial products, including disadvantages stemming from regulatory frameworks of various jurisdictions, compatibility with mouth rinse formulation, staining effects on tooth surface, and substantivity to oral surfaces.

Accordingly, there remains a need in the art for new oral compositions that reduce or prevent plaque formation whilst overcoming the above disadvantages.

SUMMARY OF THE INVENTION

The above objectives are achieved via oral care compositions comprising polymers formed from the reaction of xylitol with polycarboxylic acids, anhydrides, esters or acid halides thereof and optionally arginine.

Accordingly this application envisions a number of oral care compositions comprising polymers of types (A) and (B):

Type (A) are those polymers formed via grafting with xylitol and optionally arginine to a preformed polymer according to structure (I, I', and I");

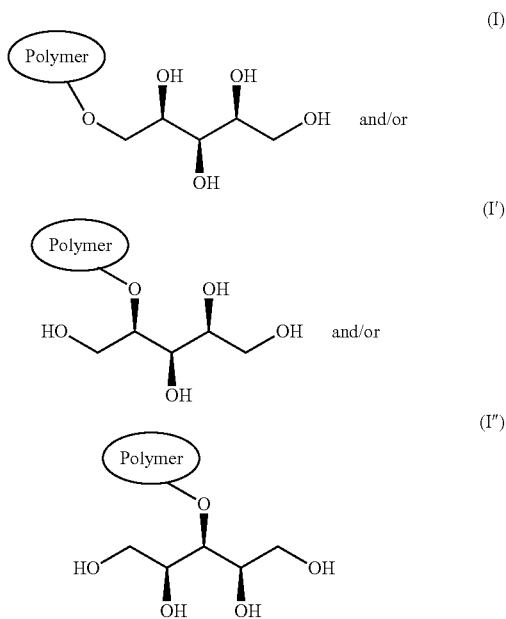

The xylitol retains its stereochemistry.

The polymers of type (A) are particularly useful as thickeners.

Type (B) are those polymers formed via reaction with the condensants xylitol and polycarboxylic acids, esters, anhydrides or acid halides thereof compounds and optionally arginine where the condensants makeup the backbone of the formed polymer.

The formed polymers (A and B) are characterized by biofilm inhibition, biofilm disruption, inhibition of bacterial acid production and substantivity to oral tissues and tooth surfaces. Those polymers of type (B) which further contain arginine are useful for reducing tooth sensitivity.

Thus the present application is directed to oral care composition comprising polymers formed from xylitol;

polycarboxylic acids, anhydrides, esters or acid halides compounds or polymeric polycarboxylic acids, anhydrides, esters or acid halides thereof, and optionally arginine;

wherein the formed polymer is distributed in an orally acceptable carrier.

The above oral care composition may comprise a polymer (A) formed by reacting polymeric polycarboxylic acids, anhydrides, esters or acid halides thereof comprising pendant carboxylic acid, anhydride or esters groups with xylitol to form a xylitol functionalized polymer of the formulae (I, I', I")

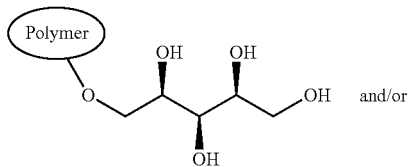

(I)

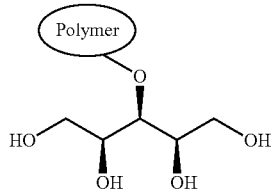

(I″)

wherein the formed polymer(s) is distributed in an orally acceptable carrier.

Furthermore envisioned is an oral care composition comprising a polymer (B) containing a backbone and the backbone of the polymer is formed from Xylitol, polycarboxylic acids, anhydrides, esters or acid halides thereof compounds, and optionally arginine, wherein the formed polymer is distributed in an orally acceptable carrier.

An oral care composition comprising polyesteramide formed from xylitol, arginine and a polycarboxylic acid, anhydride, ester or acid halide thereof represented by the structures II, II', II″) below are claimed and believed to be novel.

(I')

-continued

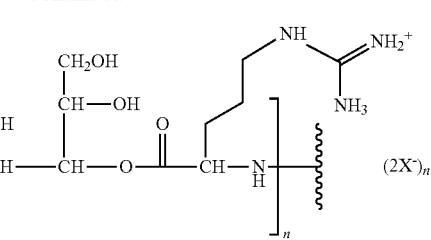
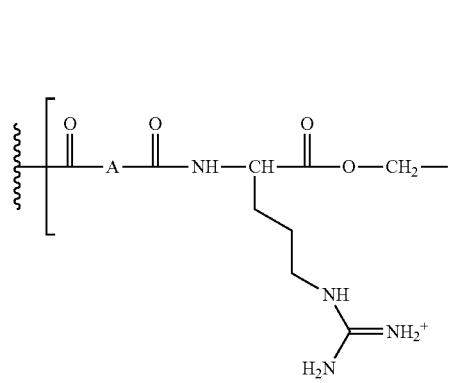

(II″)

(2X⁻)$_n$

A is a linear or branched unsubstituted $C_1$-$C_{20}$ alkylene or a linear or branched $C_1$-$C_{20}$ alkylene substituted by C(O)OR$^1$, O(O)O⁻ or OH;

or

A is a linear or branched unsubstituted $C_1$-$C_{20}$ alkylene interrupted by —O— or NR$^2$— or a linear or branched $C_1$-$C_{20}$ alkylene substituted by C(O)OR$^1$, C(O)O⁻ or OH;

wherein R$^1$ is hydrogen, unsubstituted linear or branched $C_1$-$C_{20}$ alkylene, linear or branched $C_1$-$C_{20}$ substituted by C(O)OR$^1$, C(O)O⁻ or OH and R$^2$ is hydrogen, linear or branched $C_1$-$C_{20}$ alkylene substituted by C(O)OH or OH;

X is any organic or inorganic orally acceptable anion. Normally the number of positive charges on the polyguanidiniums will equal the negative charges for X⁻;

and n is an integer ranging from 2 to 5000.

This application also encompasses a number of methods:

Inhibiting bacterial plaque in the oral cavity by contacting the oral epithelial tissues and/or teeth of a mammal with a composition comprising polymers formed from the xylitol;

polycarboxylic acids, anhydrides, esters or acid halides compounds or polymeric polycarboxylic acids, anhydrides, esters or acid halides thereof, and optionally arginine, and the formed polymer is distributed in an orally acceptable carrier.

Retarding or preventing the acid production from oral bacteria comprising the step of contacting the oral epithelia tissues and/or teeth of a mammal with an oral care composition comprising a polymer formed from xylitol, polycarboxylic acids, anhydrides, esters or acid halides compounds or polymeric polycarboxylic acids, anhydrides, esters or acid halides thereof, and optionally arginine.

and the formed polymer is distributed in an orally acceptable carrier.

Disrupting a biofilm in an oral cavity by contacting the oral epithelial tissues and/or teeth of a mammal with an oral care composition comprising a therapeutically effective amount of a polymer formed from xylitol, polycarboxylic acids, anhydrides, esters or acid halides compounds or polymeric polycarboxylic acids, anhydrides, esters or acid halides thereof, and optionally arginine;

and the formed polymer is distributed in an orally acceptable carrier.

Reducing dental sensitivity comprising applying to a surface of a mammalian tooth an oral care composition comprising a polymer formed from the condensation of xylitol, polycarboxylic acids, anhydrides, esters or acid halides compounds or polymeric polycarboxylic acids, anhydrides, esters or acid halides thereof, and arginine and the formed polymer is distributed in an orally acceptable carrier.

Sweetening an oral care composition by adding a polymer to the oral care composition wherein the polymer is formed from the condensation of xylitol, polycarboxylic acids, anhydrides, esters or acid halides compounds or polymeric polycarboxylic acids, anhydrides, esters or acid halides thereof, and optionally arginine.

Thickening an oral care composition by adding thereto a polymer according to polyesters of type (A) or (B) above.

Also envisioned are a number of uses of polymers formed from xylitol, polycarboxylic acids, anhydrides, esters or acid halides compounds or polymeric polycarboxylic acids, anhydrides, esters or acid halides thereof, and optionally arginine;

wherein the formed polymer is distributed in an orally acceptable carrier:

To inhibit bacterial plaque in the oral cavity,

To disrupt biofilm and/or retard acid production from oral bacterial in an oral cavity, To reduce dental sensitivity of a mammalian tooth Or To sweeten or thicken an oral care composition. It is also believed that the xylitol arginine di esters and salts thereof are novel. Thus the intermediates are claimed per se:

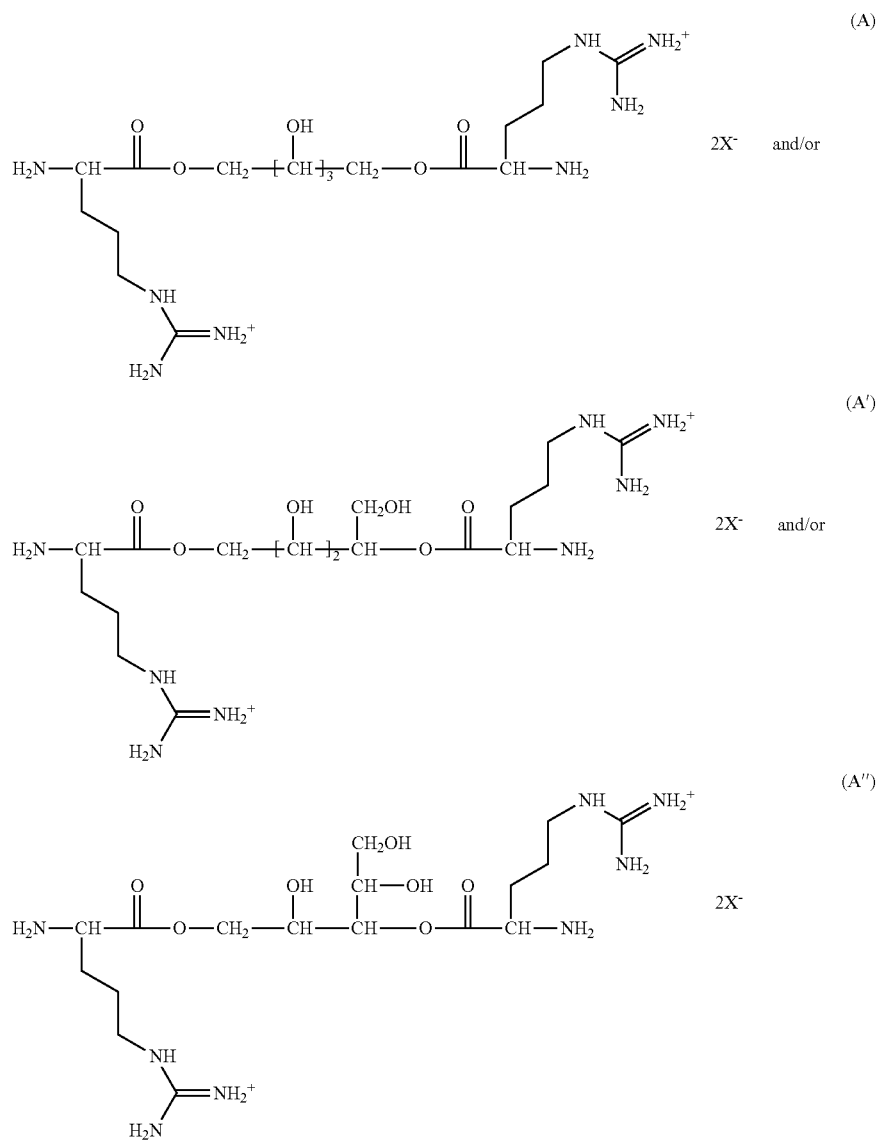

Furthermore, oral care compositions comprising the polyesters or polyesteramides described above are envisioned wherein the composition is a product selected from the group consisting of orally dissolvable films, whitening strips, mouthwashes, tooth pastes, dentifrices, oral lozenges, chewing gums and dental flosses.

DETAILED DESCRIPTION OF THE INVENTION

Oral Care

As used herein, the term "oral care" refers to both therapeutic and prophylactic treatment of diseases and disorders affecting the oral cavity or associated medical conditions. Oral diseases and disorders include, but are not limited to: plaque, dental caries; periodontal diseases (e.g., gingivitis, adult periodontitis, early-onset periodontitis, etc.); mucosal infections (e.g., oral candidiasis, herpes simplex virus infections, recurrent aphthous ulcers, etc.); oral and pharyngeal cancers; and precancerous lesions.

Orally Acceptable Carrier

The term "orally acceptable carrier" includes any conventional oral delivery system, such as dental care products, food products and chewing gum. Examples of dental care product may include but are not limited to, films (i.e. whitening strips, dissolvable mouth wash strips), dentifrices, topical solutions or pastes such as toothpastes, mouthwashes in the form of liquids or sprays or slurries, powders, gels or tablets and dental flosses. Examples of food products which may contain oral compositions described herein include, but are not limited to, lozenges, chewing gums and confections.

Molecular Weight

When the term molecular weight is used this will normally indicate a weight average molecular weight ($M_w$) unless otherwise indicated.

Comprising

Comprising for purposes of the invention is open ended, that is other components may be included. Comprising is synonymous with containing or including.

Condensants

Condensants for purposes of this application means molecules which come together to form a covalent bond by eliminate water, alcohol or a conjugate acid such as HCL. Normally the condensants are for example multifunctional alcohols, amines, acids, acid halides, esters or anhydrides. A $C_1$-$C_{20}$ glycol will condense with an alkyl diacid to form a polyester while a diamine will condense with a diacid to form a polyamide. Therefore the applicants include anhydrides as possible condensants although water is already eliminated when the anhydride is formed. An acid halide or acid chloride will condense with xylitol to eliminate for example HCL.

Biofilm

As used herein, the term "biofilm" refers to the film formed from the attachment of microorganisms to surfaces and the subsequent development of multiple layers of cells.

Dental Plaque

As used herein, the term "dental plaque" refers to the diverse microbial community (predominantly bacteria) found on the tooth surface, embedded in a matrix of polymers of bacterial and salivary origin. Plaque is used synonymously with biofilm.

Inhibition

As used herein, the term "inhibition" refers to at least a decrease of dental plaque-associated bacterial growth and/or biofilm formation.

Xylitol

Xylitol is represented by the structure

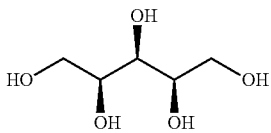

Xylitol has long been known as a sweetener or a substitute for sucrose or glucose. It is also well known to affect the growth of different strains of *Streptococcus mutans* and inhibit acid production which leads to reduced caries formation. See Waler, S. M et al, *Scand. J. Dent Res.* 1983, 91, pages 253-259 and DE 2606533.

Polymeric Polycarboxylic Acids, Anhydrides, Esters or Acid Halides Thereof,

Type (A) Polyesters

As mentioned above the oral compositions may contain type (A) polyesters. These polymers are formed from polymeric polycarboxylic acids, anhydrides, esters or acid halides thereof which are polymeric compounds which comprise pendant carboxylic acid, anhydride, esters or acid halide which groups are reacted with xylitol and optionally arginine.

The polymeric compounds (which form polymers of type A) comprising pendant carboxylic acid, anhydride, ester or acid halide groups and are for example selected from the group consisting of alginic acid, carboxymethylcellulose, poly(meth)acrylic acid and polymaleic acid preferably alginic acid, carboxymethylcellulose and polyglutamic acid.

These polymeric compounds (which form the polymer of type A) will have a degree of acid, ester, anhydride or acid halide substitution ranging from 0.1 to 3, preferably 0.1 to 1.5.

For example carboxymethylcellulose acid substitution will range from 0.1 to 0.9 while polyalginic acid is 1 (1 acid group per repeating unit). These polymers of type A may also be used as a sweeteners and/or thickeners in oral care compositions.

Thus the use of polymer (A) of formulae (I), (I') or (I") as sweeteners or thickeners in an oral care compositions is also an embodiment of this application

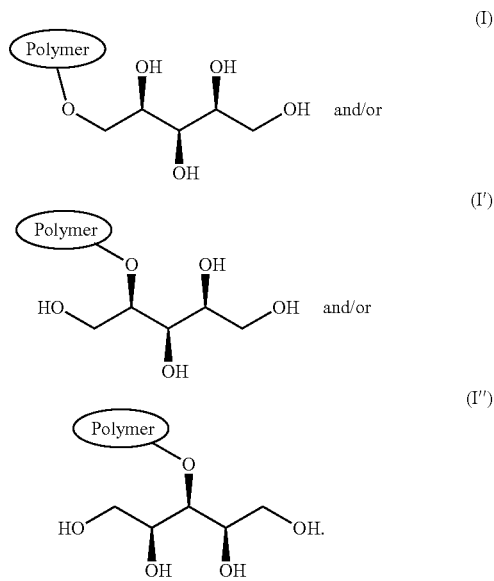

Type A polymers of particular interest are xylitol grafted alginic acid, carboxymethylcellulose, poly(meth)acrylic acid, polyglutamic acid and polymaleic acid, preferably alginic acid, polyglutamic acid, and carboxymethylcellulose.

Polycarboxylic Acids, Anhydrides, Esters or Acid Halides Thereof Compounds

Type B Polymers

Polycarboxylic acids, anhydrides, esters or acid halides thereof means for purposes of this application two or more carboxylic acids or derivatives of the two or more carboxylic acids. Thus these form type B polymers.

By derivatives it is meant that the carboxylic acid groups may be $C_1$-$C_4$ alkyl esters, substituted or unsubstituted phenyl esters, free acids, anhydrides or acid halides. This would include compounds such as dicarboxylic acids, tricarboxylic acids and tetracarboxylic acids esters, anhydrides or acid halides thereof.

The terms "polycarboxylic acids, anhydrides, esters or acid halides compounds" can be represented by the formula (III). These compounds are used in the preparation of type B polymers of xylitol, that is polymers with xylitol in the backbone of the polymer.

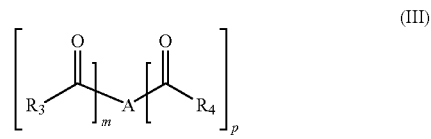

A is a linear or branched unsubstituted $C_1$-$C_{20}$ alkylene or a linear or branched $C_1$-$C_{20}$ alkylene substituted by C(O)OR$^1$, C(O)O$^-$ or OH, or A is a linear or branched unsubstituted $C_1$-$C_{20}$ alkylene interrupted by —O— or $NR^2$— or a linear or branched $C_1$-$C_{20}$ alkylene interrupted by —O— or $NR^2$ substituted by $C(O)OR^1$, $C(O)O^-$ or OH;

wherein $R^1$ is hydrogen, unsubstituted linear or branched $C_1$-$C_{20}$ alkylene, linear or branched $C_1$-$C_{20}$ alkylene substituted by C(O)OH, $C(O)O^-$ or OH and $R^2$ is hydrogen or linear or branched $C_1$-$C_{20}$ alkylene substituted by C(O)OH or OH;

m and p are 1 or 2;

and $R^3$ and $R^4$ are independently OH, halogen, $OR^5$, —OC(O) which —OC(O) is bound to A to form a cyclic anhydride or $R^3$ is oxygen and $R^4$ is a bond to the oxygen of $R^3$, $R^5$ is a $C_1$-$C_4$ alkyl or substituted or unsubstituted phenyl.

It is preferable that A is a linear or branched unsubstituted $C_1$-$C_{10}$ or a linear or branched $C_1$-$C_{10}$ alkylene substituted by C(O)OR1, $C(O)O^-$ or OH, or A is a linear or branched unsubstituted $C_1$-$C_{10}$ alkylene interrupted by $NR^2$ or a linear or branched $C_1$-$C_{10}$ alkylene interrupted by $NR^2$ substituted by $C(O)OR^1$, $C(O)O^-$ or OH and $R^2$ is hydrogen or linear or branched $C_1$-$C_{10}$ alkylene substituted by C(O)OH or OH.

Most preferably A is a linear or branched unsubstituted $C_1$-$C_8$ alkylene or a linear or branched $C_1$-$C_8$ alkylene substituted by C(O)OR1, $C(O)O^-$ and OH or A is a linear or branched $C_1$-$C_8$ interrupted by $NR^2$ and $R^2$ is $C_1$-$C_8$ alkylene substituted by C(O)OH.

$C_1$-$C_{20}$ alkylene includes $C_1$-$C_{10}$ alkylene, $C_1$-$C_8$ alkylene and $C_1$-$C_6$ alkylene.

Examples of $C_1$-$C_{20}$ alkylene dicarboxylic acids, $C_1$-$C_{20}$ alkylene tricarboxylic acids and $C_1$-$C_{20}$ alkylene tetracarboxylic acids or esters thereof are for example malonic acid, succinic acid, glutaric acid, adipic acid, pimelic acid, suberic acid, sebacic acid, azelaic acid, citric acid, isocitric acid, diglycolic acid, 1,2,3-propanetricarboxylic acid, 1,1,3,3-propanetetracarboxylic acid, 1,1,2,2-ethane tetracarboxylic acid, 1,2,3,4-butantetetracarboxylic acid, 1,2,2,3 propanetetracarboxylic acid, 1,3,3,5 pentanetetracarboxylic acid, $C_1$-$C_4$ alkyl esters thereof, acid halides thereof, anhydrides thereof such as ethylenediaminetetraacetic dianhydride and combinations thereof.

Branched or unbranched unsubstituted $C_1$-$C_{20}$ alkylene interrupted by —O— or $NR^2$— or a linear or branched $C_1$-$C_{20}$ alkylene interrupted by —O— or $NR^2$ substituted by $C(O)OR^1$, $C(O)O^-$ or OH are for example ethylenediamine tetraacetic acid, ethyleneglycolbis-tetraacetic acid, diglycolic acid, ethylenediamine tetrapropionic acid, iminodiacetic acid, 1,2-propylenediaminetetraacetic acid, N-methyl, -ethyl, -propyl and -butyl iminodiacetic acid, 1,3-propylenediaminetetraacetic acid, N-hydroxyethylethylenediaminetriacetic acid, triethylenetetraminehexaacetic acid and diethylenetriaminepentaacetic acid.

The $C_1$-$C_{20}$ alkylene di, tri or tetra carboxylic acids may be substituted by hydroxy. Examples of hydroxyl substituted $C_1$-$C_{20}$ alkylene dicarboxylic acids, tricarboxylic acids and tetracarboxylic acids are malic acid, tartronic acid, citric acid, isocitric acid, tartaric acid and mucic acid, $C_1$-$C_4$ alkyl esters thereof, acid halides thereof, anhydrides thereof and combinations thereof.

Important examples of anhydrides are succinic anhydride, glutaric anhydride, adipic anhydride, pimelic anhydride, acetyl citric anhydride, the anhydride of diglycolic acid, the mono and dianhydrides of propanetetracarboxylic acid, the mono or dianhydrides of butanecarboxylic acid and ethylenediaminetetraacetic dianhydride are of particular interest.

Thus the polycarboxylic acid, esters, anhydrides and halides may for example be selected from the group consisting of malonic acid, succinic acid, glutaric acid, adipic acid, pimelic acid, suberic acid, sebacic acid, azelaic acid, citric acid, 1,2,3-propanetricarboxylic acid, 1,1,3,3-propanetetracarboxylic acid, 1,1,2,2-ethane tetracarboxylic acid, 1,2,3,4-butantetetracarboxylic acid, 1,2,2,3 propanetetracarboxylic acid, 1,3,3,5 pentanetetracarboxylic acid, malic acid, tartronic acid, isocitric acid, tartaric acid, mucic acid, ethylenediamine tetraacetic acid, ethyleneglycolbis-tetraacetic acid, diglycolic acid, ethylenediamine tetrapropionic acid, iminodiacetic acid, 1,2-propylenediaminetetraacetic acid, N-methyl, -ethyl, -propyl and -butyl iminodiacetic acid, 1,3-propylenediaminetetraacetic acid, N-hydroxyethylethylenediaminetriacetic acid, triethylenetetraminehexaacetic acid and diethylenetriaminepentaacetic acid, $C_1$-$C_4$ alkyl esters, substituted or unsubstituted phenyl esters, acid halides and anhydrides thereof.

A preferable listing of polycarboxylic acids, esters or anhydride is malonic acid, succinic acid, glutaric acid, adipic acid, citric acid, isocitric acid, tartaric acid, mucic acid, diglycolic acid, ethylenediaminetetraacetic acid or $C_1$-$C_4$ alkyl esters thereof, anhydrides (i.e. ethylenediaminetetraacetic dianhydride for example) thereof, acid halides thereof and combinations thereof.

Type B polymer of particular interest are:

polyesters of xylitol and citric acid, $C_1$-$C_4$ alkyl esters, acid halides or anhydride thereof of formulae (IV, IV', IV'', IV''')

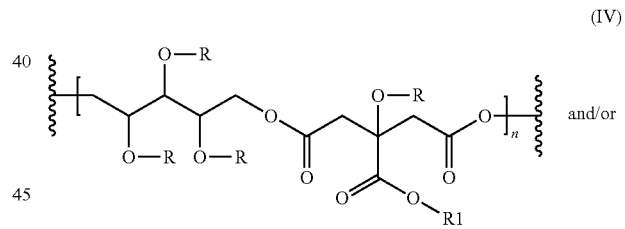

(IV)

and/or

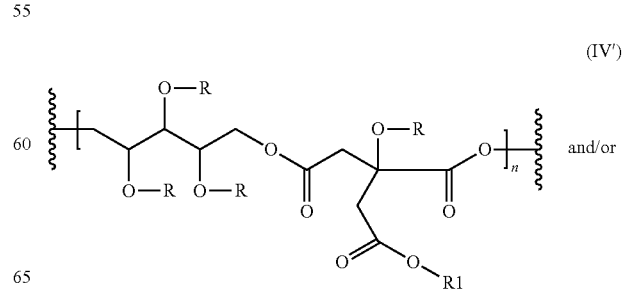

(IV')

and/or (IV″)

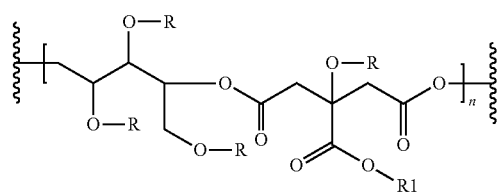

and/or (IV‴)

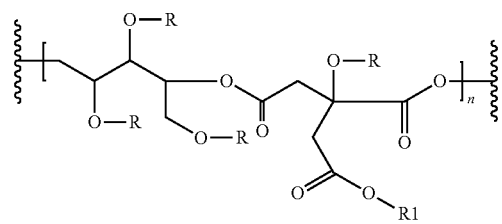

and/or

R = H, citric acid, or polymer chain
R1 = H, xylitol, or polymer chain wherein n is a number from 1 to 5000, preferably 2 to 3000;

polyester of xylitol and ethylenediaminetetraacetic acid (EDTA), esters or anhydrides thereof as in formulae (V, V' or V"):

(V)

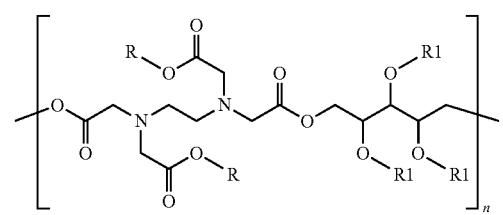

and/or (V')

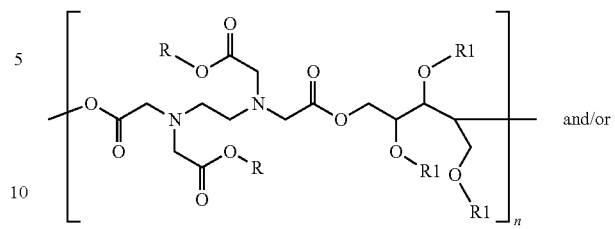

and/or (V")

R = H or xylitol residue
R1 = H or EDTA residue wherein EDTA is ethylenediaminetetraacetic acid and n is 1, 2 or 3 to 5,000, preferably 3 to 3000;

polyesters of xylitol and succinic acid, $C_1$-$C_4$ alkyl or substituted or unsubstituted phenyl esters or anhydride thereof;

polyester amides of xylitol, arginine and succinic acid terpolymers;

polyester amides of xylitol, arginine and ethylenediaminetetraacetic acid or diahydride thereof terpolymers;

and polyester amides of xylitol, arginine and citric acid terpolymers.

Arginine

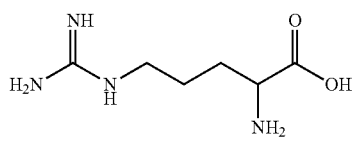

Arginine is an amino acid. When arginine is reacted with xylitol, the free acid arginine will effectively condense to form an ester bond. Arginine may be incorporated into either type A or B xylitol containing polymer but are most typically formed from type B polymers described above.

Arginine will for example be condensed with xylitol to form an arginine endcapped xylitol. This endcapped xylitol can then be reacted with a polycarboxylic acid, ester or anhydride to form a polyesteramide terpolymer of the structures (II, II', II").

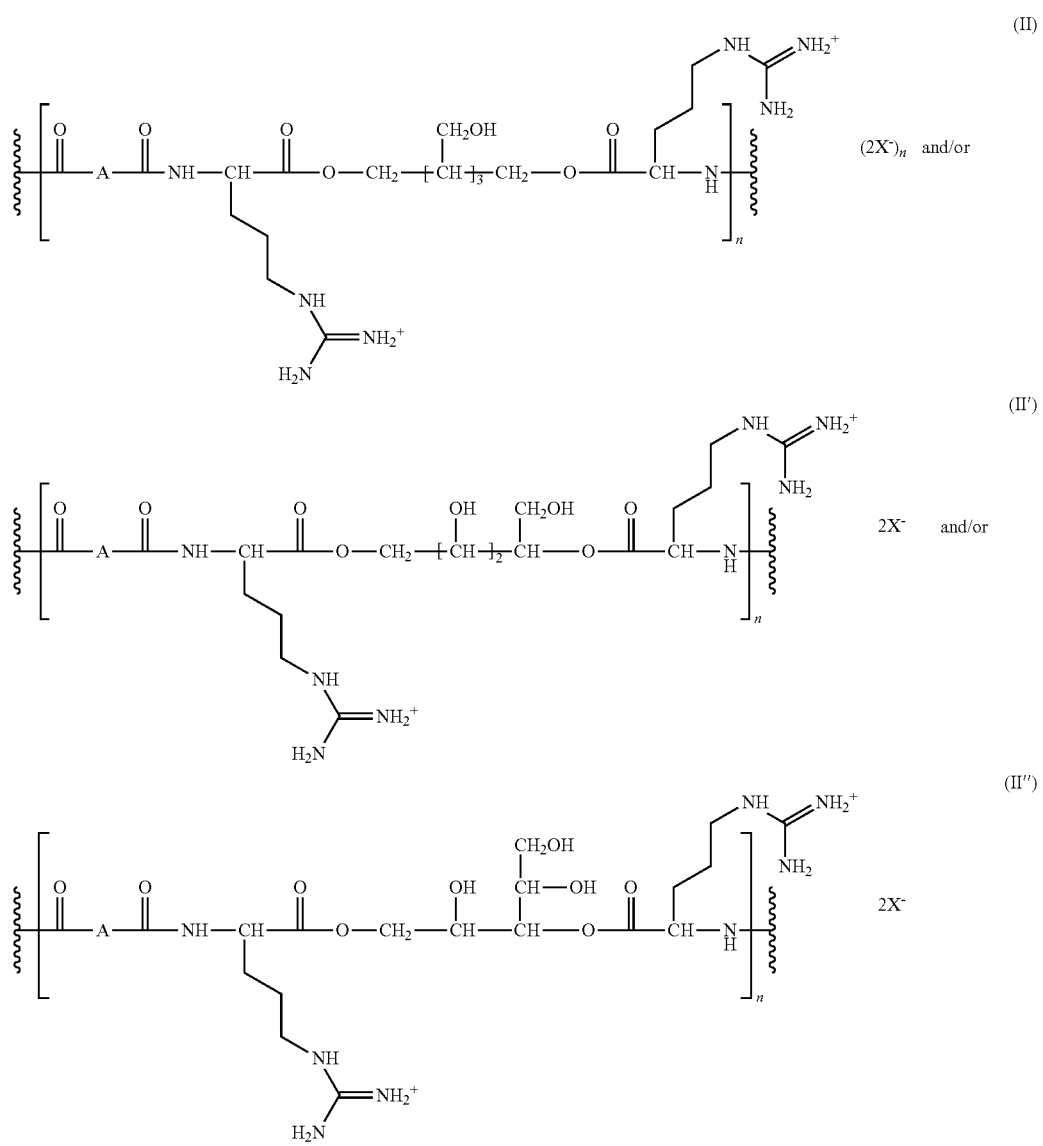

A is a linear or branched unsubstituted $C_1$-$C_{20}$ alkylene or a linear or branched $C_1$-$C_{20}$ alkylene substituted by $C(O)OR^1$, $C(O)O^-$ or OH;
or
A is a linear or branched unsubstituted $C_1$-$C_{20}$ alkylene interrupted by —O— or $NR^2$— or a linear or branched $C_1$-$C_{20}$ alkylene substituted by $C(O)OR^1$, $C(O)O^-$ or OH;

wherein $R^1$ is hydrogen, unsubstituted linear or branched $C_1$-$C_{20}$ alkylene, linear or branched $C_1$-$C_{20}$ substituted by $C(O)OR^1$, $C(O)O^-$ or OH and $R^2$ is hydrogen or linear or branched $C_1$-$C_{20}$ alkylene substituted by C(O)OH or OH;

X is any organic or inorganic orally acceptable anion. For example $X^-$ may be phosphate, phosphonate, carbonate, bicarbonate, chloride, bisulfate, sulfate, formate, acetate, citrate, oxalate, tartrate, glycolate, gluconate, malate, ascorbate and ethylenediaminetetraacetic acid and envisioned.

Normally the number of positive charges on the polyguanidiniums will equal the negative charges for $X^-$; and n is an integer ranging from 1,2 or 3 to 5,000. Preferably n is 3 to 3,000.

It is preferable that A is a linear or branched unsubstituted $C_1$-$C_{10}$ or a linear or branched $C_1$-$C_{10}$ alkylene substituted by C(O)OR1, $C(O)O^-$ or OH,
or
A is a linear or branched unsubstituted $C_1$-$C_{10}$ alkylene interrupted by $NR^2$ or a linear or branched $C_1$-$C_{10}$ alkylene interrupted by $NR^2$ substituted by $C(O)OR^1$, C(O) $O^-$ or OH, $R^2$ is hydrogen or linear or branched $C_1$-$C_{10}$ alkylene substituted by C(O)OH or OH.

Most preferably A is a linear or branched unsubstituted $C_1$-$C_8$ alkylene or a linear or branched $C_1$-$C_8$ alkylene substituted by C(O)OR1, $C(O)O^-$ and OH
or
A is a linear or branched $C_1$-$C_8$ interrupted by $NR^2$ and $R^2$ is $C_1$-$C_8$ alkylene substituted by C(O)OH.

Polymers incorporating xylitol into the backbone of the formed polyester of particular interest are:

Polyesters of xylitol, citric acid and $C_1$-$C_4$ alkyl esters, substituted or unsubstituted phenyl esters or anhydride thereof of formulae (IV, IV', IV" and/or IV'");

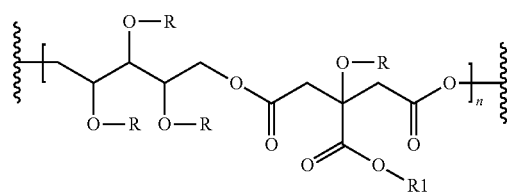
(IV)
and/or

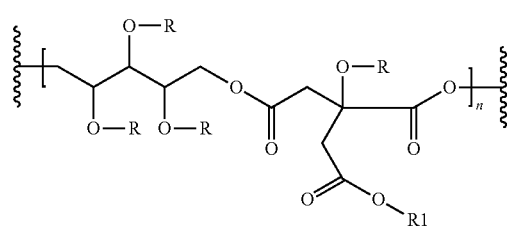
(IV')
and/or

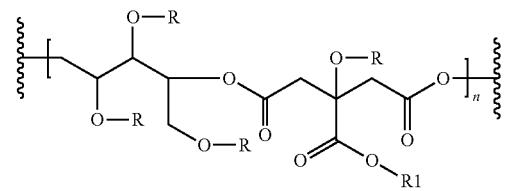
(IV'')
and/or

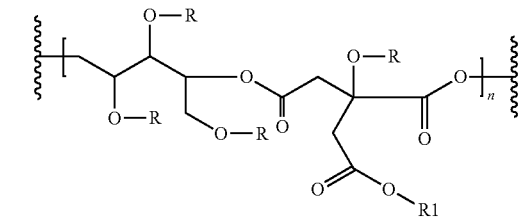
(IV''')

R = H, citric acid, or polymer chain
R1 = H, xylitol, or polymer chain

Polyesters of xylitol and ethylenediaminetetraacetic acid, esters or anhydrides thereof as in formulae (V, V', and/or V''):

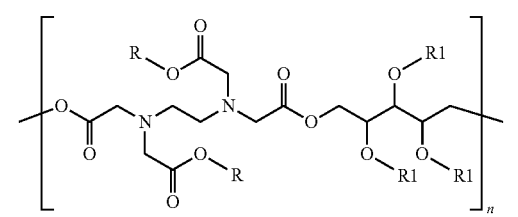
(V)
and/or

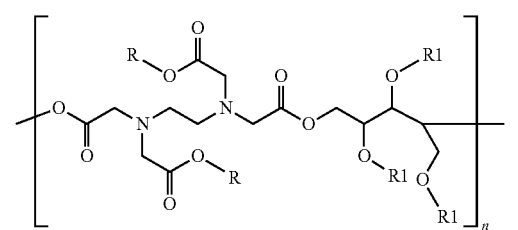
(V')
and/or

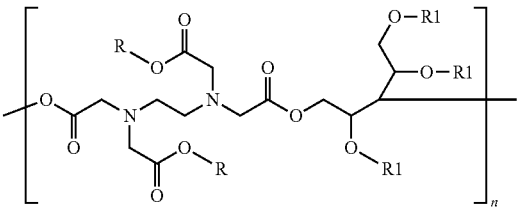
(V'')

R = H or xylitol residue
R1 = H or EDTA residue

*EDTA is ethylenediaminetetraacetic acid or ethylenediaminetetraacetic acid dianhydride of tetracarboxylic acid;

Polyesters of xylitol and succinic acid, $C_1$-$C_4$ alkyl esters, substituted or unsubstituted phenyl esters or anhydride thereof;

Arginine may be included as a comonomer or condensant of any of the described xylitol containing polymers such as polymers of structures (IV) and (V).

Arginine terpolymers of particular interest are:

Polyester amides of xylitol, arginine and succinic acid terpolymers;

Polyester amides of xylitol, arginine and ethylene diamine tetracarboxylic acid (or diahydride thereof) terpolymers Polyester amides of xylitol, arginine and citric acid terpolymers.

These arginine containing polymer above, may be used to reduce tooth sensitivity.

The formed xylitol grafted polymer will vary in weight average Mw from 500 to about 1,000,000, preferably from about 1000 to about 800,000 and most preferably about 1500 to about 500,000.

For example, the condensation product of xylitol and alginic acid (VI) is of interest.

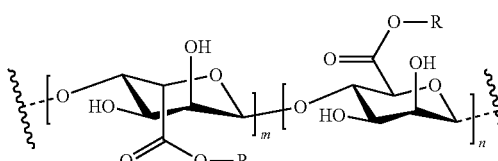
(VI)

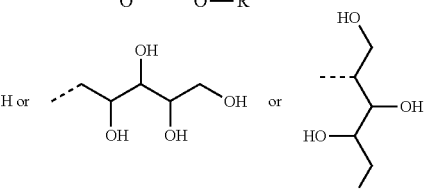
R = H or

or

The degree of acid substitution on the alginic acid is about 1.

The condensation product of xylitol and carboxymethylcellulose (the free acid) (VII) is also of particular interest.

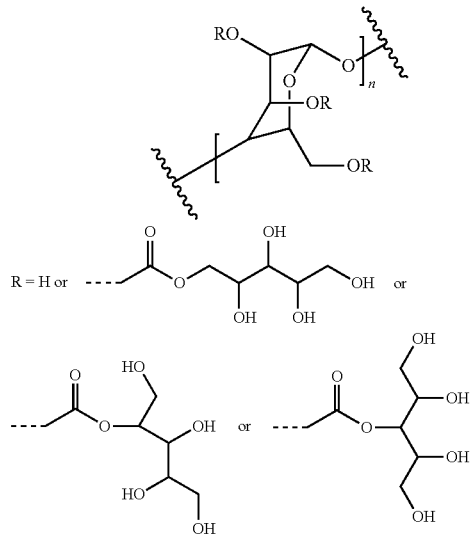

(VII)

The degree of acid substitution of the carboxymethylcellulose varies from about 0.1 to about 3, preferably about 0.5 to about 2.0.

Type A and B Formed Polymers from Xylitol

The oral care composition of the application will contain formed polyester (A or B type) of the xylitol-polycarboxylic acid (or ester or anhydride) and optionally arginine containing polymer and will have a Mw ranging from about 500 to about 700,000, preferably from about 1000 to about 250,000, most preferably about 1500 to about 150,000.

The oral care composition according to the application will contain formed polymers (type A or B), wherein xylitol makes up from about 3 to about 80 wt. %, preferably about 4% to about 75 wt %, most preferably 5 wt. % to about 65 wt. % based on the total weight of the formed polymer.

The oral care composition will comprise about 0.01 to about 95 wt. %, preferably about 0.1 to about 50 wt. %, most preferably about 0.2 to about 20 wt. % of the formed polymer based on the total weight of the oral care composition.

These applications as explained above include not only oral care compositions but various Methods. For example:

inhibiting bacterial plaque in the oral cavity by contacting the oral epithelial tissues and/or teeth of a mammal with an oral care composition comprising the polymer formed from
xylitol,
polycarboxylic acids, anhydrides, esters or acid halides compounds or polymeric polycarboxylic acids, anhydrides, esters or acid halides thereof,
and
optionally arginine,
and the formed polymer is distributed in an orally acceptable carrier;

retarding or preventing acid production from oral bacteria comprising the step of contacting the oral epithelia tissues and/or teeth of a mammal with an oral care composition comprising a polymer formed from,
xylitol,
polycarboxylic acids, anhydrides, esters or acid halides compounds or polymeric polycarboxylic acids, anhydrides, esters or acid halides thereof,
and
optionally arginine
and the formed polymer is distributed in an orally acceptable carrier;

disrupting a biofilm in an oral cavity by contacting the oral epithelial tissues and/or teeth of a mammal with a composition comprising the oral care composition comprising the polymer formed from
xylitol,
polycarboxylic acids, anhydrides, esters or acid halides compounds or polymeric polycarboxylic acids, anhydrides, esters or acid halides thereof,
and
optionally arginine,
and the formed polymer is distributed in an orally acceptable carrier.

The oral care composition of this application may of course contain a number of other ingredients. For example in addition to the xylitol containing polymers or the application the oral care composition may contain ingredients such as excipients, flavoring agents, antimicrobial agents, anti-caries agents, dentifrice vehicles, surfactants, humectants, antioxidants, light stabilizers, anti-tartar agents or thickening agents.

Excipients

In some embodiments, an oral care composition in accordance with the present invention includes at least one excipient. Excipients suitable for use in the present invention include any compound that is conventionally used in oral care compositions.

Suitable excipients for an oral composition in accordance with the present invention may be chosen from: preservatives, abrasives (smoothing agents), further antibacterial agents, inflammation-inhibiting agents, irritation-preventing agents, irritation-inhibiting agents, further antimicrobial agents, antioxidants, binders, (mineral) fillers, buffers, carrier materials, chelating agents (chelate formers), cleaning agents, care agents, surface-active substances, emulsifiers, enzymes, foam-forming agents, foam stabilizers, foam boosters, gelling agents, gel-forming agents, bleaching agents, smell- and/or taste-modulating agents, smell- and/or taste-reducing agents, smell- and/or taste-enhancing agents, plasticizers, (mucous membrane)/skin cooling agents (cooling substances), (mucous membrane)/skin soothing agents (mucous membrane)/skin cleansing agents, (mucous membrane)/skin care agents, (mucous membrane)/skin healing agents, mucous membrane-protecting agents, stabilizers, suspending agents, vitamins, colorants, color-protecting agents, pigments, surfactants, electrolytes, silicone derivatives, polyols, calcium carbonate, calcium hydrogen phosphate, aluminum oxide, fluorides, zinc, tin, potassium, sodium and strontium salts, pyrophosphates, hydroxyapatites.

In some embodiments, an oral care composition in accordance with the present invention includes at least one excipient, wherein the at least one excipient is chosen from: surfactants, desensitizing agents, whitening agents, tartar control agents, antibacterial agents, abrasives, chelants including silica, binders and thickening agents, detergents, adhesion agents, foam modulators, pH modifying agents, mouth-feel agents, sweeteners, flavoring agents, colorants, preservatives, combinations thereof, and the like.

Flavoring Agents

In some embodiments, an oral care composition in accordance with the present invention includes a flavoring agent. In some embodiments, the flavoring agent is a member chosen from: mucous membrane cooling agents, mucous membrane warming agents, sharp-tasting substances, sweeteners, sugar substitutes, organic or inorganic acidifiers (e.g., malic acid, acetic acid, citric acid, tartaric acid, phosphoric acid), bitter principles (e.g., quinine, caffeine, limonine, amarogentine, humulones, lupolones, catechols, tannins), edible mineral salts (e.g., sodium chloride, potassium chloride, magnesium chloride and sodium phosphates), essential oils (e.g., oils of spearmint, peppermint, wintergreen, sassafras, clove, sage, eucalyptus, marjoram, cinnamon, lemon, lime, grapefruit, and orange), menthol, carvone, anethole, and combinations thereof.

The xylitol polymers of types (A) and (B) are especially suitable as sweetening agents in oral care compositions.

As taught above this application embodies a method of slowly releasing xylitol (a sweetener) to an oral cavity by applying an oral composition to the oral cavity and the oral compositions comprises polymers formed from
xylitol;
polycarboxylic acids, anhydrides, esters or acid halides compounds or polymeric polycarboxylic acids, anhydrides, esters or acid halides thereof,
and optionally arginine;
wherein the formed polymer is distributed in an orally acceptable carrier.

Abrasives

Abrasives suitable for use in the present invention include silica materials and particularly silica gels and precipitated amorphous silica having an oil absorption value of less than 100 cc/100 g silica and preferably in the range of from 45 cc/100 g to less than 70 cc/100 g silica. Oil absorption values are measured using the ASTM Rub-Out Method D281. Low oil absorption silica abrasives particularly useful in the practice of the present invention are marketed under the trade designation Sylodent® XWA (Davison Chemical Division of W. R. Grace & Co., Baltimore, Md. 21203). Sylodent® 650 XWA, a silica hydrogel composed of particles of colloidal silica having a water content of 29% by weight averaging from 7 to 10 microns in diameter, and an oil absorption of less than 70 cc/100 g of silica is a preferred example of a low oil absorption silica abrasive useful in the practice of the present invention. Another low oil absorption silica abrasive particularly useful in the practice of the present invention is marketed under the trade designation DP-105.TM. (J. M. Huber Chemicals Division, Havre de Grace, Md. 21078) is a precipitated amorphous silica having an average particle size distribution from 5 to 12 microns and an oil absorption in the range of 50 to 70 cc/100 g. Other abrasives which may be used in the practice of the present invention include precipitated silicas having a mean particle size of up to 20 microns, such as Zeodent® 115, (J. M. Huber Chemicals Division, Havre de Grace, Md. 21078), or Sylodent® 783 (Davison Chemical Division of W. R. Grace & Company), sodium metaphosphate, potassium metaphosphate, tricalcium phosphate, dihydrated dicalcium phosphate, aluminum silicate, calcined alumina, bentonite or other siliceous materials, or combinations thereof.

In some embodiments, an oral care composition in accordance with the present invention includes an abrasive excipient. In some embodiments, the abrasive excipient is a silica material. In some embodiments, the silica material is colloidal particles having an average particle size ranging from 3 microns to 12 microns. In some embodiments, the colloidal particles have an average particle size ranging from 5 to 10 microns and a pH range from 4 to 10 preferably 6 to 9 when measured as a 5 wt. % slurry. In some embodiments, the silica material is a low oil absorption silica abrasive. In some embodiments, the low oil absorption silica abrasive is present in the oral care compositions of the present invention at a concentration of 5 wt. % to 40 wt. %. In some embodiments, the low oil absorption silica abrasive is present at a concentration of 10 wt. % to 30 wt. %.

In some embodiments, the abrasive excipient is a member chosen from: silicic acids, calcium carbonates, calcium phosphates, aluminium oxides and/or hydroxyapatites, sodium metaphosphate, potassium metaphosphate, tricalcium phosphate, dihydrated dicalcium phosphate, aluminum silicate, calcined alumina, bentonite, surface-active substances (e.g., sodium lauryl sulfate, sodium lauryl sarcosinate, and cocamidopropylbetaine), and other siliceous materials, and combinations thereof.

In some embodiments, the abrasive excipient may be used individually as the sole abrasive in preparing an oral care composition of the present invention or in combination with other known dentifrice abrasives. In some embodiments, the total quantity of abrasive excipient present in the dentifrice compositions of the present invention is 5 wt. % to 60 wt. %. In some embodiments, the abrasive excipient is present in an amount of 10 wt. % to 55 wt. % by weight when the dentifrice composition is a toothpaste.

Anti-Microbial Agents

Anti-microbial agents suitable for use in the present invention include nonionic antibacterial agents, including halogenated diphenyl ether compounds such as 2,4,4'-trichloro-2'-hydroxydiphenyl ether (Triclosan) and 2,2'-dihydroxy-5,5'-dibromodiphenyl ether. Other useful nonionic antibacterial agents include phenolic compounds including phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference.

In some embodiments, an oral care composition in accordance with the present invention includes an anti-microbial agent. In some embodiments, the anti-microbial agent is a member chosen from: triclosan, chlorhexidine and its salts (e.g., its acetate, gluconate or hydrochloride), peroxides, phenols and their salts, domiphen bromide (phenododecinium bromide), bromochlorophene, Zn salts, stannous fluoride, chlorophylls, Cu salts, Cu gluconate, Cu chlorophyll, sodium lauryl sulfate, polylysine, quarternary monoammonium salts such as cocoaliphaticbenzyldimethylammonium chloride, homopolymers of arginine, arginine salts or complexes, or also pyridinium salts such as cetyl pyridinium chloride, and combinations thereof.

Thymol, menthol, methyl salicylate and eucalyptol and mixtures thereof are well known as antimicrobials and active against plaque.

In some embodiments, the anti-microbial agent is a nonionic antibacterial agent. In some embodiments, the nonionic antibacterial agent is included in a dentifrice composition at a concentration of 0.001 wt. % to 5 wt. %. In some embodiments, the nonionic antibacterial agent is present in an amount of 0.01 wt. % to 1.5 wt. %.

Anti-microbial agents of particular interest are quarternary monoammonium salts such as cocoaliphaticbenzyldimethylammonium chloride or also pyridinium salts such as cetyl pyridinium chloride, polylysine, thymol, menthol, methyl salicylate and eucalyptol triclosan, chlorhexidine and its salts (e.g., its acetate, gluconate or hydrochloride) and combinations thereof.

Anti-Caries Agents

In some embodiments, an oral composition in accordance with the present invention includes an anti-caries agent. In some embodiments, the anti-caries agent is a fluoride ion source chosen from: inorganic fluoride salts, such as soluble alkali metal, alkaline earth metal salts (e.g., sodium fluoride, stannous fluoride, potassium fluoride, ammonium fluoride, calcium fluoride), a copper fluoride such as cuprous fluoride, zinc fluoride, barium fluoride, sodium fluorosilicate, ammonium fluorosilicate, sodium fluorozirconate, ammonium fluorozirconate, sodium monofluorphosphate, aluminum mono- and di-fluorophosphate, fluorinated sodium calcium pyrophosphate, and combinations thereof.

Dentifrice Vehicles

In some embodiments, an oral care composition in accordance with the present invention includes an orally-acceptable dentifrice vehicle. In some embodiments, the dentifrice vehicle includes a humectant therein. Humectants suitable for use in the present invention include glycerin, sorbitol, xylitol, and/or propylene glycol of molecular weight in the range of 200 to 1,000. As used herein, "sorbitol" refers to the material typically commercially available as a 70% aqueous solution. In some embodiments, the humectant concentration is from 5 wt. % to 70 wt. % of the oral composition.

In some embodiments, an oral care composition in accordance with the present invention includes water. Water employed in the preparation of commercially suitable toothpastes should preferably be deionized and free of organic impurities. In some embodiments, water is present in an amount of 15 wt. % to 30 wt. % of the oral composition. In some embodiments, water is present in an amount of 10 wt. %. In some embodiments, these amounts of water include the free water which is added in addition to that which is introduced with other materials such as with sorbitol.

Surfactants

Surfactants suitable for use in the compositions of the present invention include any material able to achieve increased prophylactic action and render the oral care compositions more cosmetically acceptable. The surfactant is preferably a detersive material that imparts to the oral care composition detersive and foaming properties.

In some embodiments, an oral care composition in accordance with the present invention includes a surfactant. In some embodiments, an oral care composition in accordance with the present invention includes a combination of surfactants.

In some embodiments, an oral care composition in accordance with the present invention includes a surfactant. In some embodiments, an oral care composition in accordance with the present invention includes a combination of surfactants. In some embodiments, the surfactant is an anionic surfactant including higher alkyl sulfates such as sodium lauryl sulfate, sodium laureth sulfate, N-alkyl amides of glutamates such as sodium cocoyl glutamate, esters of ethoxylated fatty alcohol and citric acid such as laureth-7 citrate, and mono- and/or dialkyl sulfosuccinates such as sodium laureth sulfosuccinate.

In some embodiments, the surfactant is an enzyme-compatible surfactants chosen from: nonionic polyoxyethylene surfactants such as Poloxamer 407 and 335. These poloxamers are triblock copolymers composed of a central hydrophobic chain of polyoxypropylene(poly(propylene oxide)) flanked by two hydrophilic chains of polyoxyethylene (poly(ethylene oxide)). A further nonionic surfactant of interest is polyethylene glycol ethers of long chain fatty acids such as stearic acid for example Steareth 3.

Polysorbate 20 is a polyoxyethylene derivative of sorbitan monolaurate, which is distinguished from the other members in the polysorbate range by the length of the polyoxyethylene chain and the fatty acid ester moiety and is useful in oral care compositions.

Polyalkyl glucosides are also of interest. They are derived from sugars and fatty alcohols. Examples or polyalkyl glucosides are lauryl glucoside, decyl glucoside, caprylyl/capryl glucoside and coco glucoside to name a few.

Amphoteric surfactants such as cocamidopropyl betaine and cocamidopropyl betaine lauryl glucoside are also of interest. In some embodiments, an oral composition in accordance with the present invention includes a surfactant or a combination of surfactants at a total surfactant concentration in the dentifrice composition of 2 wt. % to 10 wt. %. In some embodiments, the surfactant or combination of surfactants is present in an amount of 3.5 wt. % to 6.5 wt % by weight.

Anti-Tartar Agents

In some embodiments, an oral care composition in accordance with the present invention includes an anti-tartar agent. In some embodiments, the anti-tartar agent is chosen from: pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, sodium tripolyphosphate; long chain polyphosphates such as sodium hexametaphosphate; and cyclic phosphates such as sodium trimetaphosphate. In some embodiments, an anti-tartar agent is present in a dentifrice composition of the present invention at a concentration of 1 wt. % to 5 wt. %.

Desensitizing Agents

In some embodiments, the oral care composition may further contain desensitizing agents. For Example nitrate salt, a bicarbonate salts, potassium nitrate, arginine-bicarbonate-phytate complex, potassium citrate or oxalate and arginine may be added to the oral composition in combination with the presently disclosed terpolymers.

Furthermore, this application is directed to a method of reducing dental sensitivity comprising applying to a surface of a mammalian tooth an oral care composition comprising a polymer formed from the condensation of
xylitol,
polycarboxylic acids, anhydrides, esters or acid halides compounds or polymeric polycarboxylic acids, anhydrides, esters or acid halides thereof,
and
arginine and the formed polymer is distributed in an orally acceptable carrier.

Thickening Agents

In some embodiments, an oral care composition in accordance with the present invention includes a thickening agent. In some embodiments, the thickener is selected from the group consisting of, but not limited to: calcium carbonate, titanium dioxide, silicon dioxide, talcum, aluminium oxide, dicalcium phosphate, tricalcium phosphate, magnesium hydroxide, cellulose thickeners such as carboxymethyl cellulose, hyroxyalkyl celluloses such as hydroxypropyl cellulose hydroxyethyl cellulose, gums such as xanthan gum, polyglycols and polyethylene glycol, inorganic thickeners (e.g., amorphous silica compounds, natural and synthetic clays, lithium magnesium silicate and magnesium aluminum silicate), and combinations thereof.

In some embodiments, the thickening agent is an organic thickener chosen from: natural and synthetic gums and colloids including cellulose thickeners such as carboxymethyl cellulose; hyroxyalkyl celluloses such as hydroxypropyl cellulose hydroxyethyl cellulose; gums such as xanthan gum; polyglycols of varying molecular weights sold under the tradename Polyox™; and polyethylene glycol. In some embodiments, the thickening agent is an inorganic thickener chosen from: amorphous silica compounds such as colloidal silicas compounds available under the trade designation Cab-o-Sil® (manufactured by Cabot Corporation and distributed by Lenape Chemical, Bound Brook, N.J.); Zeodent® 165 (J.M. Huber Chemicals Division, Havre de Grace, Md. 21078); Sylodent® 15 (Davison Chemical Division of W.R. Grace Corporation, Baltimore, Md. 21203); natural and synthetic clays; lithium magnesium silicate (Laponite); and magnesium aluminum silicate (Veegum). In some embodiments, the thickening agent is present in a dentifrice composition of the present invention in amounts of 0.1 wt. % to 10 wt. %. In some embodiments, the thickening agent is present in an amount of 0.5 wt. % to 4.0 wt. %.

The xylitol polymers of type (A) are of particular use as thickening agents. For example, The condensation product of xylitol and carboxymethylcellulose (the free acid) (VII)

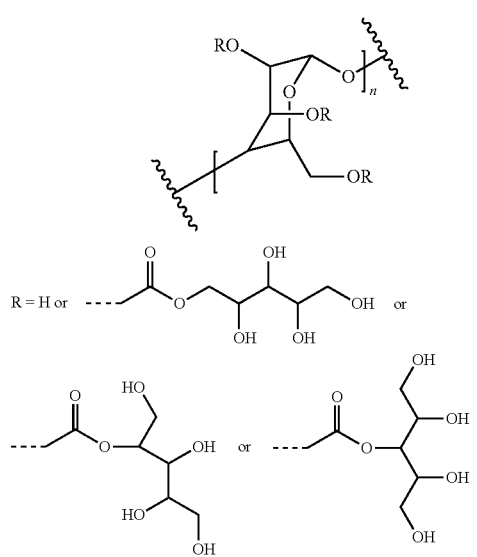

(VII)

wherein the degree of acid substitution of the carboxymethylcellulose varies from about 0.1 to about 3, preferably about 0.5 to about 2.0 makes an ideal thickener in oral care compositions, and the condensation product of xylitol and alginic acid (VI) are of interest as a thickeners for oral care compositions

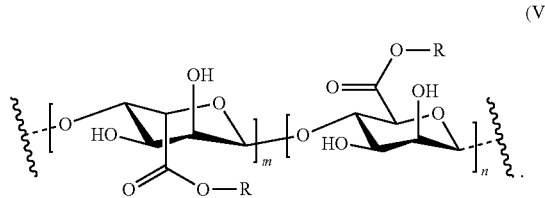

(VI)

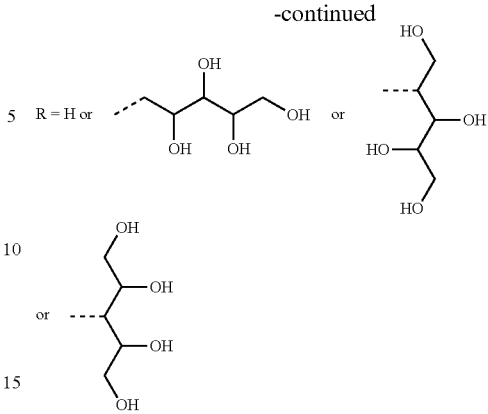

Anti-Oxidants

In some embodiments, an oral composition in accordance with the present invention includes an anti-oxidant. In some embodiments, the anti-oxidant is chosen from: naturally occurring tocopherols and their derivatives (e.g., Vitamin E acetate), Vitamin C and its salts and derivatives (e.g., ascorbyl palmitate, Mg ascorbyl phosphate, ascorbyl acetate), Vitamin A and derivatives (Vitamin A palmitate), tocotrienols, flavonoids, alpha-hydroxy acids (e.g., citric acid, lactic acid, malic acid, tartaric acid) and their Na, Ka and Ca salts, flavonoids, quercetin, phenolic benzylamines, propyl gallate, octyl gallate, dodecyl gallate, butylhydroxyanisole (BHA, E320), butylhydroxytoluene (BHT, 2,6-di-tert.-butyl-4-methylphenol, E321), lecithins, mono- and diglycerides of edible fatty acids esterified with citric acid, carotenoids, carotenes (e.g., α-carotene, β-carotene, lycopene) and their derivatives, phytic acid, lactoferrin, EDTA, EGTA), folic acid and its derivatives, ubiquinone and ubiquinol and their derivatives, ferulic acid and its derivatives, zinc and its derivatives (e.g., ZnO, $ZnSO_4$), selenium and its derivatives (e.g., selenium methionine), orthophosphates and Na, K and Ca salts of mono-phosphoric acids, and constituents, extracts and fractions thereof isolated from plants, (e.g., tea, green tea, algae, grapeseeds, wheat germ, chamomile, rosemary, oregano), and combinations thereof.

Antioxidants of particular interest are octadecyl 3-(2,5-di-tert-butyl-4-hydroxyl phenyl propionate, tetrabutyl ethylidinebisphenol and tetrakis (3-(3,5-di-tert-butyl-4-hydroxyphenyl)propionate.

Light stabilizers may also be included in the oral care compositions. A good example of a Benzotriazole light stabilizers is 2-(5-chloro-2H-benzotriazol-2-yl)-6-(1,1dimethylethyl)-4-methyl phenol.

Of particular interest are oral care composition comprising the xylitol polymer described above wherein the oral care composition comprises at least one excipient selected from the group consisting of surfactants, desensitizing agents, chelating agents, whitening agents, tartar control agents, antibacterial agents, abrasives including silica, binders and thickening agents, detergents, adhesion agents, foam modulators, pH modifying agents, mouth-feel agents, antioxidants, light stabilizers, sweeteners, flavoring agents, colorants, preservatives and combinations thereof.

The oral care composition comprising the xylitol polymer described above will preferably be combined with an antibacterial agent selected from the group consisting of triclosan, chlorhexidine and its salts (e.g., its acetate, gluconate or hydrochloride), peroxides, phenols and their salts, domiphen bromide (phenododecinium bromide), bromochlorophene, Zn salts, chlorophylls, Cu salts, Cu gluconate, Cu chlorophyll, sodium lauryl sulfate, quarternary monoammonium salts such as cocoaliphaticbenzyldimethylammonium chloride or also pyridinium salts such as cetyl pyridinium chloride, polylysine and combinations thereof, quarternary monoammonium salts such as cocoaliphaticbenzyldimethylammonium chloride or also pyridinium salts such as cetyl pyridinium chloride, polylysine, triclosan, stannous fluoride, homopolymers of arginine and salts of arginine, chlorhexidine and its salts (e.g., its acetate, gluconate or hydrochloride), homopolymers of arginine, arginine complexes or salts and combinations thereof.

Evaluation of Xylitol Polymers

The xylitol polymers are evaluated using a number of different criteria:

Prevention of Biofilm Development

Multispecies Saliva Biofilms:

Hydroxy apatite (HA) coated surfaces of a 96 peg lid (Biosurface Technologies, Boseman, Mont.) are pellicle treated with pooled human saliva 200 μl/per well of a 96 well clear plate for 30 minutes at 37° C. aerobically. Into each well of the growth plate, clear 96 well plate, 160 μl inoculated Brain Heart Infusion (BHI) broth is added. Test solutions are added to a desired final concentration and water is added to bring the final volume to 200 μl. The hydroxyl apatite coated pegs are added to.

S. mutans Biofilms:

S. mutans 25175 is inoculated into 10 mL BHI and incubated statically at 37° C. overnight. Then the culture is inoculated to OD 0.1 into Jordans 5% sucrose as the growth media. Hydroxy apatite coated peg lids are pellicle treated with sterile artificial saliva 200 ul/per well of a 96 well clear plate for 30 minutes at 37° C. aerobic. Into each well of the growth plate, clear 96 well plate, 160 ul innoculated Jordans 5% sucrose broth is added. Test solutions are added to a desired final concentration and water is added to bring the final volume to 200 ul. The pegs are added to the growth plate and incubated for 24 hr anaerobically at 37° C.

the growth plate and incubated for 24 hr anaerobically at 37° C.

After 24 hr of growth time, pegs containing biofilms are transferred to a 96 well clear rinse plate containing 200 ul of sterile BHI or Sterile Jordans 5% sucrose for 5 minutes at room temperature. The pegs are then transferred to a white 96 well plate containing 200 ul of Bac-titer-Glo: this is incubated at room temperature for 10 minutes (shaking) and read for luminescence using a plate reader.

Substantitivity Compared to Xylitol Condensant Alone

Method to evaluate the substantivity of polymers to hydroxyl apatite surfaces and the effects these polymers have on the growth of Streptococcus mutans and Saliva derived biofilms.

For Multispecies Saliva Biofilms:

Hydroxy apatite (HA) coated surfaces are pellicle treated with pooled human saliva 200 ul/per well of a 96 well clear plate for 30 minutes at 37° C. aerobically. Fresh human saliva is inoculated in Jordan's 5% sucrose at OD 0.17.

For S. mutans Biofilms:

S. mutans (ATCC #25175) is inoculated into 10 mL BHI and incubated statically at 37° C. overnight. Then the culture is inoculated to OD 0.21 into Jordans 5% sucrose as the growth media. Hydroxy apatite coated peg lids are pellicle treated with sterile artificial saliva 200 ul/per well of a 96 well clear plate for 30 minutes at 37° C. aerobic.

The peg lids are transferred to a clear 96 well plate containing 200 ul of the designated treatments below in Jordan's with 5% sucrose. This peg/plate assembly is shaken for 5 mins and then incubated for 25 mins aerobically at 37 C.

After 30 mins of treatment the two pegs are transferred to a 96 well plate containing 200 ul of water and it is rinsed for 10 min at 500 rpm. After 10 mins, the pegs are transferred to a plate containing 200 ul of the S. mutans culture or saliva and incubated for 24 hrs.

After incubation the peg lids are transferred to a rinse plate containing 200 ul of water for 5 minutes and then transferred to white 96 well plate containing 200 ul Bac-titer-Glo, this is shaken for 5 minutes and read for luminescence.

Method for Evaluating Disruption of Established Biofilms

Method to screen combinations of actives, example polymers and chelates to identify potential synergies for biofilm disruption.

Polystyrene Pegs are pellicle treated with fresh pooled human saliva for 30 minutes at 37° C. aerobically. Saliva is inoculated into BHI broth at a final concentration of 10% saliva. 200 ul of inoculated or uninoculated media is added to each well. The pegs are added to the growth media and incubated anaerobically 37° C.

At 24 hr. the pegs are removed and transferred to a fresh plate containing 200 ul of sterile BHI. And incubated anaerobically for another 24 hr at 37 C.

After 48 hr of growth time, pegs containing the biofilms are transferred to a 96 well rinse plate containing 200 ul of or BHI. Following a 5 minute rinse at room temperature, the pegs are transferred to a treatment plate containing combinations of actives, chelate and polymers. This is followed a 5 minute treatment (shaking at 500 rpm). The treated pegs are transferred to a white 96 well plate containing 200 ul Bac-titer-Glo reagent—this is incubated at room temperature for 5 minutes (shaking) and read on a plate reader for luminescence.

Inhibition of Bacterial Acid Production

Method to observe the acid production of S. mutans in a medium containing a pH indicator and glucose. Observe how xylitol and the example polymers affect acid production. A culture of S. mutans (ATCC #25175) is grown statically overnight in 10 mL liquid broth (BHI) at 37° C. This culture is inoculated into fresh Bromo Cresol Purple (BCP) broth at 10%.

20 uL of 10% pH adjusted test solutions are added to each well of a clear 96 well plate. The no treatment control has 20 ul water added. To each experimental well 180 of the inoculated BCP broth is added. To the no inoculum control 20 ul water and 20 ul filter sterilized overnight culture broth are added.

The plate is shaken at 500 rpm for 5 minutes and then read for absorbance at both 588 nm (Absorption max at pH 6.8—purple) and 427 nm (Absorption max at pH 5.2—yellow). Both wavelengths are measured every hour for several hours but before evaporation became an issue. The plates are shaken for 10 seconds before reading.

Method for Determining Enzymatic Degradation of Xylitol Polymer by Oral Enzymes

The method for determining enzymatic breakdown of polymer is determined by Sigma Quality Control Test Procedure: Enzymatic Assay of Esterase. This assay however, exchanges Ethyl Butyrate solution with solution of test polymer. pH change is monitored over time as an indicator of esterase activity and polymer degradation.

Example 1

Experimental Procedure for Preparation of Xylitol-Citric Acid Polymer

A mixture of 15.2 grams of xylitol and 19.2 grams of citric acid in a 500 ml single neck flask attached to a short-path rotary distillation apparatus is heated at 120° C. under vacuum at 50 torr. The resultant melt is heated for 6 hours and 3.5 grams of water is collected. Upon cooling to ambient temperature 31 grams of a colorless solid is obtained. The polymer is dissolved into deionized water with addition of sodium bicarbonate to obtain a 10% solution of pH 7.

Example 2

Experimental Procedure for Preparation of Xylitol-Alginic Acid Polymer

A mixture of 10 grams of xylitol and 11.6 grams of alginic acid in a 250 ml single neck flask attached to a short-path rotary distillation apparatus is heated at 140° C. under vacuum at 50 torr. The resultant melt is heated for 5 hours and 1.1 grams of water is collected. Upon cooling to ambient temperature the resultant solid is mixed with 100 mL of deionized water and centrifuged. The supernatant is dialyzed (3500 molecular weight cutoff membranes) with deionized water and freeze dried to obtain 2.24 grams off-white powder. The polymer is dissolved into BHI medium and Jordan's medium with addition of 2N sodium hydroxide solution to obtain 2% solutions of pH 7.

Example 3

Experimental Procedure for Preparation of Xylitol-Carboxymethyl Cellulose Polymer In a 500 ml 3-neck flask, 100 g of xylitol is melted under a nitrogen atmosphere at 120° C. To the resultant molten xylitol is added 2.08 grams of carboxymethyl cellulose while raising the temperature to 170° C. at a rate to maintain a stirrable reaction melt. The reaction melt is stirred under a nitrogen sweep to facilitate removal of the water of reaction. After 7 hours the reaction mixture is cooled to ambient temperature and the reaction mass is dissolved into 200 ml of deionized water. The resultant solution is dialyzed (3500 molecular weight cutoff membranes) with deionized water and freeze dried to obtain 2.4 grams off-white powder. The polymer is dissolved into BHI medium and Jordan's medium with addition of 2N sodium hydroxide solution to obtain 2% solutions of pH 7.

Example 4

Experimental Procedure for Preparation of Xylitol-EDTA Polymer

In a 50 ml 3-neck flask, 6.09 g of xylitol is melted under a nitrogen atmosphere at 120° C. To the resultant molten xylitol is added 2.56 grams of ethylenediamine tetraacetic acid dianhydride. After addition of the dianhydride is complete the reaction temperature is raised to 130° C. The reaction melt is stirred under a nitrogen atmosphere for 12 hours, then cooled to ambient temperature and dissolved into 50 ml of deionized water. The resultant solution is dialyzed (3500 molecular weight cutoff membranes) with deionized water and freeze dried to obtain 3.95 grams off-white powder. The polymer is dissolved into deionized water with addition of 2N sodium hydroxide solution to obtain a 10% solution of pH 7.

Example 5

Experimental Procedure for the Preparation of bis(p-nitrophenyl) Succinate.

In a 1 L 3-neck flask, equipped with an overhead stirrer, addition funnel and thermometer, is dissolved 40.0 g (0.288 mole) of p-nitrophenol in 500 mL of acetone under a nitrogen atmosphere. To the resultant bright yellow solution is added 29.1 g (0.288 mole) of triethylamine. The resultant yellow solution is cooled to 5° C. and a solution of 21.2 g of succinoyl dichloride in 100 mL of acetone is added dropwise over a 1.5 hr period, an exotherm is noted during the addition. Upon completion of the addition the brown-red suspension is stirred at 5° C. for an additional hour and then allowed to warm to ambient temperature and stirred overnight. The resultant brown-purple suspension is added 1 g of succinoyl dichloride and stirred an additional 30 minutes at ambient temperature. Added 500 mL of deionized water and stirred at ambient temperature for 15 minutes. The product is isolated by filtration and the solid is washed with water and dried at 25 in Hg/55° C. in a vacuum oven to give 45 g brown-dark red powder. The product is purified by recrystallization from ethyl acetate to give 42 g of a bright brown powder.

Example 6

Experimental Procedure for the Preparation of bis(L-arginine) Xylitol Diester

In a 2 L 4-neck flask, equipped with a Dean-stark trap, an overhead stirrer and thermometer, is added 17.4 g (0.1 mole) of L-arginine, 7.6 g (0.05 mole) of xylitol, 40 g (0.21 mole) of p-toluenesulfonic acid monohydrate and 1 L toluene under an argon atmosphere. The resultant mixture is heated at 110° C. for 16 hr and 5.5 mL of water is collected. Upon cooling the reaction mixture a yellow oil separated and the toluene layer is decanted. The yellow oil is dissolved in isopropanol at 70° C., cooled to 4° C., and decanted isopropanol. The isopropanol treatment is repeated 2 additional times. The product is dried on a rotary evaporator to give 50 g of a white powder.

Example 7

Experimental Procedure for the Preparation of arginine-xylitol-succinic Acid Polymer In a 50 ml round bottom flask is added 14 g (12.2 mmole) of tetra-p-toluenesulfonic acid salt of bis(L-arginine) xylitol diester, 4.4 g (12.2 mmole) bis(p-nitrophenyl) succinate and 14 g of dimethylsulfoxide under a nitrogen atmosphere. The mixture is mixed on a vortex mixer to form a brown solution and then heated at 75° C. To the resultant reaction mixture is added dropwise 2.7 g (26.8 mmole) of triethylamine. The resultant yellow solution is heated at 75° C. for 48 hr under nitrogen then cooled to ambient temperature. To the resultant reaction mixture is added 3 mL of ethyl acetate, stirred, and the supernatant decanted. Dissolved polymer in methanol, precipitated into ethyl acetate and decanted supernatant. The methanol/ethyl acetate precipitation procedure is repeated 2 additional times and the product is dried on a rotary evaporator to obtain 7.4 g of a yellow-brown powder.

The polymer is purified by dialysis using a 3500 molecular weight cutoff membrane with a pH 7 buffer and freeze dried to obtain a white powder. A 10% aqueous solution of the polymer is prepared and the pH adjusted to 7.

Example 8

Experimental Procedure for Preparation of arginine-xylitol-EDTA Polymer

In a 500 ml 3-neck flask, equipped with an overhead stirrer and thermocouple, is dissolved 5.75 g (5 mmole) of tetra-p-toluenesulfonic acid salt of bis(L-arginine) xylitol diester in 35 ml of anhydrous dimethylformamide under an argon atmosphere. To the resultant solution is added sequentially 1.28 grams (5 mmole) of ethylenediamine tetraacetic acid dianhydride, then 5 ml of anhydrous triethylamine. The resulting mixture is heated at 50° C. for 6 hr, then cooled to ambient temperature. Volatiles are removed under reduced pressure at 10 torr, 60° C. for 1 hr. The concentrated reaction mixture is dissolved into 100 ml of deionized water. The resultant solution is dialyzed (3500 molecular weight cutoff membranes) with deionized water and freeze dried to obtain 2.3 grams off-white powder. The polymer is dissolved into deionized water with addition of 2N sodium hydroxide solution to obtain a 10% solution of pH 7.

Example 9

Experimental Procedure for Preparation of arginine-xylitol-citric Acid Polymer

In a 250 ml 3-neck flask, equipped with an overhead stirrer, a nitrogen gas inlet and a distillation take-off, is dissolved 8.82 g (10 mmole) of dihydrochloride di-p-toluenesulfonic acid salt of bis(L-arginine) xylitol diester in 70 ml of anhydrous dimethylformamide under a nitrogen sweep. To the resultant solution is added 1.92 grams (10 mmole) of anhydrous citric acid. After the citric acid dissolved, 10 ml of anhydrous triethylamine is added, causing a white precipitate to separate from solution. The resulting mixture is heated at 130° C. with removal of distillate as it formed. After 6 hr the reaction mixture is a clear solution and is cooled to ambient temperature. Volatiles are removed under reduced pressure at 12 torr, 60° C. for 0.5 hr and then at 0.1 torr, 120° C. for 1 hr. The concentrated reaction mixture is dissolved into 250 ml of deionized water. A 140 ml portion of the resultant solution is dialyzed (3500 molecular weight cutoff membranes) with deionized water and freeze dried to obtain 0.43 grams beige powder. The polymer is dissolved into deionized water with addition of 2N sodium hydroxide solution to obtain a 10% solution of pH 7.

Example 10

Experimental Procedure for Preparation of arginine-xylitol-citric Acid Polymer (Random)

In a 250 ml 3-neck flask, equipped with an overhead stirrer, a nitrogen gas inlet and a distillation take-off, is heated a mixture of 1.52 grams (10 mmole) of xylitol, 2.11 grams (10 mmole) of L-arginine hydrochloride and 1.92 grams (10 mmole) of anhydrous citric acid at 130° C. under a nitrogen sweep. Water of reaction is removed as it formed. After 3 hr at 130° C. the reaction temperature is raised to 140° C. and the reaction mixture pressure is reduced to 50 torr for an additional 1.5 hr. The reaction melt is cooled under argon and dissolved into 50 ml of deionized water. The water solution is filtered (medium glass frit); then is dialyzed (3500 molecular weight cutoff membranes) with deionized water and freeze dried to obtain 1.28 grams off-white powder. The polymer is dissolved into deionized water with addition of 2N sodium hydroxide solution to obtain a 10% solution of pH 7.

APPLICATION EXAMPLES

Prevention of Biofilm Formation:

Polymers are evaluated using the biofilm prevention method indicated above for both *S. mutans* and multispecies saliva derived biofilm.

We observed that the polymer examples tested performed as well as or better than the combinations of the condensant controls at similar concentrations. This observation is consistent for the prevention of both the *S. mutans* and saliva biofilms (See Table 1 and Table 2).

The composition of the xylitol-citric acid polymer is 1:1 mole ratio and 44% xylitol and 56% citric acid by weight based on the total weight of the formed polymer.

The composition of the xylitol-EDTA polymer is 1:1 mole ratio and 37% xylitol and 63% EDTA by weight based on the total weight of the formed polymer.

The composition of the xylitol, arginine and succinic acid polymer is 1:2:1 xylitol:arginine:succinic acid by moles and 25% xylitol, 56% arginine and 19% succinic acid by weight based on the total weight of the formed polymer.

The composition of the xylitol succinic acid polymer is 1:1 xylitol:succinic acid by moles and 56% xylitol and 44% succinic acid by weight.

TABLE 1

Prevention of *Streptoccus mutans* biofilm development. Values are presented as percent reduction from the untreated control.

| | | Concentration of polymer or respective control | | |
|---|---|---|---|---|
| Material tested | Controls | 2.0% | 1.0% | 0.5% |
| Sterile control | 100% | | | |
| Untreated control | — | | | |
| 2% xylitol Control | −1% | | | |
| Citric Acid-xylitol polymer | | 98%[a] | 94%[a] | 40% |
| Citric Acid & xylitol Control | | 6% | 30% | 28% |
| EDTA-xylitol polymer | | 99%[a,b] | 96%[a,b] | 64% |
| EDTA & xylitol control | | 35% | −10% | −33% |
| Arginine-Succinic acid-Xylitol polymer | | 63%[a] | 55%[b] | 41% |
| Arginine & Succinic acid & Xylitol control | | 77%[a] | 35% | −37% |
| Succinic acid-xylitol polymer | | 91%[a] | 65%[a,b] | 65%[a,b] |
| Succinic acid & xylitol control | | 21% | 22% | 38% |

[a] = comparison to 2% xylitol control (p < 0.001)
[b] = comparison to respective component control (p < 0.001)

TABLE 2

Prevention of multispecies saliva biofilm development. Values are presented as percent reduction from the untreated control.

| | | Concentration of polymer or respective control | | |
|---|---|---|---|---|
| Material tested | Controls | 2.0% | 1.0% | 0.5% |
| Sterile control | 100% | | | |
| Untreated control | — | | | |
| 2% xylitol Control | 17% | | | |
| Citric Acid-xylitol polymer | | 61% | 73%[a,b] | 68%[a,b] |
| Citric Acid & xylitol Control | | 60%[a] | 30% | 8% |
| EDTA-xylitol polymer | | 100%[a,b] | 92%[a,b] | 56%[a] |
| EDTA & xylitol control | | 73%[a] | 62%[a] | 42%[a] |
| Arginine-Succinic acid-Xylitol polymer | | 92%[a,b] | 80%[a,b] | 56%[a] |
| Arginine & Succinic acid & Xylitol control | | 69%[a] | 59%[a] | 35% |
| Succinic acid-xylitol polymer | | 94%[a,b] | 47%[a] | 95%[a,b] |
| Succinic acid & xylitol control | | 34%[a] | 11% | 8% |

[a] = comparison to 2% xylitol control (p < 0.001)
[b] = comparison to respective component control (p < 0.001)

Substantitivity Compared to Xylitol Condensant Alone;

Results: Polymers are evaluated using the substantivity for biofilm prevention method indicated above for both *S. mutans* and multispecies saliva derived biofilms.

Cetyl pyridinium chloride at 0.7% is used as the positive control and it demonstrates retention of activity after rinsing in the model and is considered substantive.

Xylitol-Succinic acid-Arginine polymer shows substantivity when compared to individual components at comparable concentrations.

Xylitol-EDTA shows some substantivity but controls EDTA is also substantive in this model.

The observations are consistent for the prevention of both the *S. mutans* and saliva biofilms (See Table 3 and Table 4).

TABLE 3

Multispecies saliva derived Biofilm growth after 24 hr on pre-treated hydroxyl apatite surfaces.

| | % treatment | % decrease in biofilm as compared to growth control (negative indicates increased biofilm) |
|---|---|---|
| Growth Control | — | 100% |
| No treatment control | — | 0% |
| Cetylpyridinium chloride | 0.070% | 98% |
| Xylitol Control | 1.120% | 14% |
| | 2.000% | 12% |
| EDTA control | 1.320% | 79% |
| | 0.660% | 60% |
| | 0.330% | 32% |
| | 0.165% | 25% |
| | 0.083% | 17% |
| Xylitol-EDTA polymer | 2.000% | 24% |
| | 1.000% | 10% |
| | 0.500% | 42% |
| | 0.250% | 5% |
| | 0.125% | −2% |
| Arginine control | 1.120% | 49% |
| | 0.560% | −22% |
| | 0.280% | −24% |
| | 0.140% | −20% |
| | 0.070% | −28% |
| Xylitol-Arginine-Succinic acid polymer | 2.000% | 43% |
| | 1.000% | 45% |
| | 0.500% | 49% |
| | 0.250% | 54% |
| | 0.125% | 46% |

TABLE 4

*Streptococcus mutans* Biofilm growth after 24 hr on pre-treated hydroxyapatite surfaces

| | % treatment | % decrease in biofilm as compared to growth control (negative indicates increased biofilm) |
|---|---|---|
| Growth Control | — | 100% |
| No treatment control | — | 0% |
| Cetylpyridinium chloride | 0.070% | 100% |
| Xylitol Control | 1.120% | −11% |
| | 2.000% | −15% |
| EDTA control | 1.320% | 41% |
| | 0.660% | 46% |
| | 0.330% | 44% |
| | 0.165% | 37% |
| | 0.083% | 13% |
| Xylitol-EDTA polymer | 2.000% | 25% |
| | 1.000% | 9% |
| | 0.500% | 37% |
| | 0.250% | −3% |
| | 0.125% | −5% |
| Arginine control | 1.120% | −29% |
| | 0.560% | −53% |
| | 0.280% | −59% |
| | 0.140% | −18% |
| | 0.070% | −40% |
| Xylitol-Arginine-Succinic acid polymer | 2.000% | 37% |
| | 1.000% | 29% |
| | 0.500% | 27% |
| | 0.250% | 17% |
| | 0.125% | 0% |

Disruption of Established Biofilms:

Polymers are evaluated using the Biofilm disruption model as described above.

Example polymers (xylitol-EDTA polymer and xylitol-arginine-succinic acid polymer) are combined with example actives (epsilon-polylysine and chlorhexidine) and a chelator (Ca EDTA).

Specific combinations gave significant improvement over the control combinations—see Table 5.

1000 ppm epsilon-Polylysine disrupted biofilm on its own. Combination of epsilon polylysine and 1% Arginine-xylitol-succinic acid polymer (with or without ca EDTA) give a significant benefit, see Table 5

Combination of 1% xylitol-EDTA polymer and chlorhexidine gives a significant improvement in activity over the polymer or chlorhexidine alone. Table 5

TABLE 5

Disruption of 48 hour saliva biofilms after treatment for 5 minutes.

| | Sterility control | Active, Chelate and Polymer | Active and Chelate control | Active and Polymer | Active control | Chelate and Polymer | Chelate control | Polymer | No treatment control |
|---|---|---|---|---|---|---|---|---|---|
| Active = 1000 ppm e-polylysine, Chelate = 0.1% Trilon Ca, Polymer = 1% Arginine-Xylitol-Succinic Acid Terpolymer | 100$^{a,b,c}$ | 68$^{a,b,c}$ | 31$^c$ | 80$^{a,b,c}$ | 29$^c$ | −13$^b$ | −10 | −7$^b$ | 0 |
| Active = 0.06% Chlorhexidine, Chelate = 0.1% Trilon Ca, Polymer = 1% Xylitol-EDTA polymer | 100$^{a,b,c}$ | 57$^{a,b,c}$ | 1 | 54$^{a,b,c}$ | −10 | −40 | −1 | −32 | 0 |

$^a$comparison to no treatment control (p < 0.001)
$^b$comparison to active control (p < 0.001)
$^c$comparison to polymer only control (p < 0.001)

Inhibition of Bacterial Acid Production.

Controls: No inoculum control showed very little change as would be expected. The no treatment control showed a large change demonstrating acid production. Xylitol controls minimally decreased OD 588 in a dose response and also increase minimally at OD 427 indicating acid inhibition at all concentrations tested. L-Arginine controls gave similar results as the no treatment control indicating no acid inhibiting effects. The citric acid, succinic acid and EDTA controls demonstrated no or little change demonstrating acid inhibiting effects. In this experiment, little change in pH (or similar change to xylitol control) is observed with polymers: Arginine-Xylitol EDTA polymer, Arginine-Xylitol-Citric Acid polymer.

TABLE 6

Delta values at OD 588

| Treatment | Mean Delta OD588 (stdev) |
|---|---|
| No inoculum control | 0.15 (0.06) |
| No Treatment control | 1.063 (0.132) |
| 2% Xylitol | 0.734 (0.131) |
| 1% Xylitol | 0.759 (0.081) |
| 0.5% Xylitol | 0.841 (0.119) |
| 0.1% Xylitol | 0.993 (0.099) |
| 1% L-Arginine pH 6.3 | 1.054 (0.13) |
| 1% citric acid pH 7.0 | 0.196 (0.029) |
| 1% succinic acid pH 7.4 | 0.323 (0.107) |
| 1% EDTA pH 7.0 | 0.283 (0.086) |
| 1% Arginine-Xylitol EDTA polymer pH 6.5 | 0.423 (0.045) |
| 1% Arginine-Xylitol-Citric Acid polymer pH 6.4 | 0.569 (0.039) |
| 1% Xylitol-Succinic Acid polymer | 0.915 (0.096) |
| 1% Arginine-Xylitol-Succinic Acid polymer pH 7 | 0.904 (0.038) |

Method for Determining Enzymatic Degradation of Xylitol Polymer by Oral Enzymes

Degradation of example polymers is conducted using porcine esterase. Esterase activity decreases the pH of the solution. The pH is monitored at the start and end of the assay (90 minutes). See Table 7. Both the xylitol-CMC and Xylitol-Succinic acid polymers were degraded by the esterase.

TABLE 7

| | 0.2% Ethyl Acetate (positive control) | 1% Xylitol-CarboxyMethyl Cellulose polymer | 1% Xylitol-Succinic Acid polymer | Borate Buffer (Negative control) |
|---|---|---|---|---|
| Start pH | 8.30 | 8.37 | 8.41 | 8.28 |
| End pH | 5.00 | 7.47 | 7.10 | 8.13 |

Oral Care Formulations Containing the Xylitol Polymers of the Invention

| Mouthwash | |
|---|---|
| Component | Parts by weight % |
| Glycerin | 7.5 |
| Polysorbate 80 | 0.12 |
| Ethanol | 15 |
| Sweetner combination (sorbitol, mannitol, xylitol) | 0.15 |
| Xylitol polymer of the invention | 1-5 |
| Cetyl pyridinium chloride | 0.04 |
| Benzoic acid | 0.05 |
| Color | 0.05 |
| Peppermint flavor | 0.1 |
| Water | qs to 100 |

| Mouthwash | |
|---|---|
| Component | Parts by weight % |
| Sorbitol | 10 |
| Glycerol | 10 |
| Ethanol | 15 |
| Propylene Glycol | 15 |
| Xylitol polymer of the invention | 1-5 |
| Sodium lauryl sulfate | 0.5 |
| Cetyl pyridinium chloride | 0.04 |
| Sodium methylcocyl taurate | 0.25 |
| Polyoxypropylene/polyoxyethylene block copolymer | 0.25 |
| Peppermint flavor | 0.1 |
| Water | qs to 100 |

| Peroxide Mouthwash | |
|---|---|
| Component | Parts by weight % |
| 35% $H_2O_2$ solution | 3.5-5% |
| Coolant (mint) | 0.07 |

| Peroxide Mouthwash | |
|---|---|
| Component | Parts by weight % |
| Flavor | 0.1-0.2 |
| Poloxamer 407 | 0.75 |
| Xylitol polymer of the invention | 0.5-3 |
| Glycerin | 11.0 |
| Propylene glycol | 3.0 |
| Sweetener combination (sorbitol, mannitol) | 0.08 |
| Cetyl pyridinium chloride | 0.1 |
| Sodium citrate | 0.2 |
| Water | qs to 100 |

| Toothpaste Formulation | |
|---|---|
| Component | Parts by weight % |
| Sodium bicarbonate | 40-45 |
| Tetra sodium pyrophosphate | 2.0 |
| Sorbitol | 35-40 |
| Xylitol polymer of the invention | 1-5 |
| Polyethylene glycol | 1.0 |
| Sodium carboxymethylcellulose | 0.7 |
| Sodium saccharin | 1.0 |
| Flavor | 0.8-1 |
| Sodium lauryl sulfate | 0.3 |
| Sodium lauroyl sarcosinate | 1.0 |
| Water | qs to 100 |

| Toothpaste Formulation | | |
|---|---|---|
| Ingredient | Formula A | Formula B |
| SnF2, USP | 0.45 | 0.45 |
| Zinc citrate | 0.5 | 0.5 |
| Zinc Lactate | — | — |
| Sorbitol(LRS) USP | 45 | 45 |
| Fused Silica (TecoSil 44CSS) | — | 15 |
| Silica Z119 | 2.5 | 0 |
| Silica Z109 | 12.5 | 0 |
| Hydroxyethyl cellulose (HEC Natrasol 250M) | 0.5 | 0.5 |
| CMC 7M8SF | 1.3 | 1.3 |
| Carrageenan mixture | 0.7 | 0.7 |
| Sodium lauryl sulfate (48397-002) | 4 | 4 |
| Saccharin Sodium | 0.5 | 0.5 |
| Sodium Gluconate | 1 | 1 |
| Xylitol polymer of the invention | 1-5 | 1-5 |
| Flavor | 1 | 1 |
| Water, USP | QS | QS |

| Lozenge Formulation | |
|---|---|
| Component | Parts by weight % |
| Sugar | 75-98 |
| Corn syrup | 1-20 |
| Flavor oil | 0.1-1.0 |
| Tablet lubricant | 0.1-5 |
| Xylitol polymer of the invention | 1-5 |
| Sodium salt of hydrolyzed methoxy ethylene-maleic anhydride copolymer (1:1 mw 70,000) | 0.05 |
| Water | .01-2 |

| Lozenge Formulation | |
|---|---|
| Component | Parts by weight % |
| Sodium saccharin | 0.15 |
| Flavor | 0.25 |
| Magnesium Stearate lubricant | 0.40 |
| Color | 0.01 |
| Xylitol polymer of the invention | 1-50 |
| PEG (40) Sorbitan diisostearate | 1 |
| Sodium salt of hydrolyzed methoxy ethylene-maleic anhydride copolymer (1:1 mw 70,000) | 0.30 |
| Sorbitol | qs to 100 |

| Lozenge Formulation | |
|---|---|
| Component | Parts by weight % |
| Sugar | 75-98 |
| Corn syrup | 1-20 |
| Flavor oil | 0.1-1.0 |
| Tablet lubricant | 0.1-5 |
| Xylitol polymer of the invention | 1-5 |
| Sodium salt of hydrolyzed methoxy ethylene-maleic anhydride copolymer (1:1 mw 70,000) | 0.05 |
| Water | .01-2 |

| Chewing Gum | |
|---|---|
| Component | Parts by weight % |
| Gum Base | 10-50 |
| Binder | 3-10 |
| Filler | 5-8 |
| Sorbitol, mannitol or combination | 0.1-5 |
| Xylitol polymer of the invention | 1-5 |
| Flavor | 0.1-5 |

The invention claimed is:

1. An oral care composition comprising:

a polymer formed from the condensation of only xylitol and carboxymethylcellulose or anhydrides, esters or acid halides thereof, wherein the formed polymer is distributed in an orally acceptable carrier.

2. The oral care composition according to claim 1, wherein the carboxymethylcellulose has a degree of acid substitution ranging from about 0.1 to about 3.

3. The oral care composition according to claim 1, wherein the formed polymer consists of one or more xylitol-grafted carboxymethylcellulose polymers selected from the group consisting of formula (I), (I') and (I"),

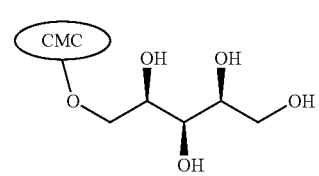
(I)

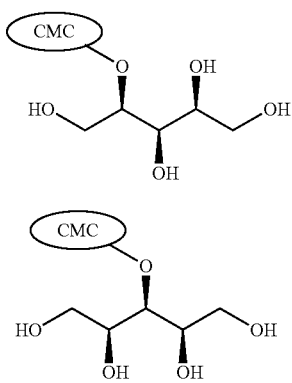

wherein CMC is a carboxymethylcellulose radical.

4. The oral care composition according to claim 2, wherein the degree of acid substitution ranges from about 0.5 to about 2.0.

5. The oral care composition according to claim 1, wherein xylitol makes up from about 3 to about 80 wt. % based on the total weight of the formed polymer.

6. The oral care composition according to claim 1, wherein the formed polymer has a Mw ranging from about 500 to about 1,000,000.

7. The oral care composition according to claim 1, comprising at least one ingredient selected from the group consisting of surfactants, desensitizing agents, chelating agents, whitening agents, tartar control agents, antibacterial agents, abrasives, binders, thickening agents, detergents, adhesion agents, foam modulators, pH modifying agents, mouth-feel agents, sweeteners, flavoring agents, colorants, preservatives and combinations thereof.

8. The oral care composition according to claim 7, wherein the ingredient is an antibacterial agent selected from the group consisting of triclosan, chlorhexidine or its salts, peroxides, phenols or their salts, domiphen bromide (phenododecinium bromide), bromochlorophene, Zn salts, chlorophylls, Cu salts, Cu gluconate, Cu chlorophyll, sodium lauryl sulfate, quaternary monoammonium salts, pyridinium salts, polylysine, homopolymers of argininine, salts or complexes of arginine, stannous fluoride, thymol, menthol, methyl salicylate, eucalyptol and combinations thereof.

9. The oral care composition according to claim 8, wherein the antibacterial agent is selected from the group consisting of quaternary monoammonium salts, pyridinium salts, polylysine, triclosan, chlorhexidine or its salts and combinations thereof.

10. The oral care composition according to claim 1, wherein the formed polymer makes up about 0.01 to about 95 wt. %, based on the total weight of the oral care composition.

11. The oral care composition according to claim 1, wherein the composition is a product selected from the group consisting of orally dissolvable films, whitening strips, mouthwashes, tooth pastes, dentifrices, oral lozenges, chewing gums and dental flosses.

* * * * *